US010889793B2

(12) United States Patent
Silverman et al.

(10) Patent No.: US 10,889,793 B2
(45) Date of Patent: Jan. 12, 2021

(54) C₁ SUBSTRATE-FED FERMENTATION SYSTEMS AND METHODS FOR PRODUCING C₄ COMPOUNDS

(71) Applicant: Calysta, Inc., Menlo Park, CA (US)

(72) Inventors: Joshua A. Silverman, Los Altos Hills, CA (US); Sol M. Resnick, Encinitas, CA (US); Drew D. Regitsky, San Francisco, CA (US)

(73) Assignee: CALYSTA, INC., Menlo Park, CA (US)

( * ) Notice: Subject to any disclaimer, the term of this patent is extended or adjusted under 35 U.S.C. 154(b) by 387 days.

(21) Appl. No.: 15/639,120

(22) Filed: Jun. 30, 2017

(65) Prior Publication Data

US 2017/0298315 A1 Oct. 19, 2017

Related U.S. Application Data

(63) Continuation of application No. 14/434,315, filed as application No. PCT/US2013/063650 on Oct. 7, 2013, now Pat. No. 10,501,714.
(Continued)

(51) Int. Cl.
*C12M 1/02* (2006.01)
*C12M 1/04* (2006.01)
(Continued)

(52) U.S. Cl.
CPC ............ *C12M 29/08* (2013.01); *C12M 23/06* (2013.01); *C12M 23/34* (2013.01); *C12M 27/24* (2013.01);
(Continued)

(58) Field of Classification Search
None
See application file for complete search history.

(56) References Cited

U.S. PATENT DOCUMENTS 3,681,200 A 8/1972 Ridgway, Jr.
3,732,148 A 5/1973 Franckowiak et al.
(Continued)

FOREIGN PATENT DOCUMENTS

CN 2205388 Y 8/1995
CN 2858636 Y 1/2007
(Continued)

OTHER PUBLICATIONS

Al Taweel et al., "Effect of Mixing on Microorganism Growth in Loop Bioreactors," *International Journal of Chemical Engineering* 2012, 12 pages.
(Continued)

*Primary Examiner* — Soren Harward
*Assistant Examiner* — Paul D. Pyla
(74) *Attorney, Agent, or Firm* — Seed IP Law Group LLP

(57) ABSTRACT

A fermenter can have at least one hollow fluid conduit disposed at least partially within a vessel. An external circumference of the hollow fluid conduit and an interior circumference of the vessel can define a downward flow path through which a multi-phase mixture including a liquid media and compressed gas substrate bubbles flows. An interior circumference of the hollow fluid conduit can defined an upward flow path which is in fluid communication with the downward flow path. The multi-phase liquid can flow through the upward flow path and exit the fermenter. Cooling may be provided in the hollow fluid conduit or the vessel. One or more backpressor generators can be used to maintain a backpressure on the fermenter. One or more fluid movers can be used to variously create an induced and/or forced flow in the downward and upward flow paths.

26 Claims, 9 Drawing Sheets

Related U.S. Application Data

(60) Provisional application No. 61/711,104, filed on Oct. 8, 2012.

(51) Int. Cl.

| | | |
|---|---|---|
| *C12M 1/08* | (2006.01) | |
| *C12P 5/02* | (2006.01) | |
| *C12P 7/16* | (2006.01) | |
| *C12P 7/18* | (2006.01) | |
| *C12P 7/40* | (2006.01) | |
| *C12P 7/42* | (2006.01) | |
| *C12P 17/02* | (2006.01) | |
| *C12N 1/08* | (2006.01) | |
| *C12N 1/10* | (2006.01) | |
| *C12N 1/12* | (2006.01) | |
| *C12N 1/20* | (2006.01) | |
| *C12N 13/00* | (2006.01) | |
| *C02F 3/32* | (2006.01) | |
| *A01G 33/00* | (2006.01) | |
| *C12M 1/00* | (2006.01) | |
| *C12M 1/12* | (2006.01) | |

(52) U.S. Cl.
 CPC ............ *C12M 29/06* (2013.01); *C12M 41/24* (2013.01); *C12P 5/02* (2013.01); *C12P 7/16* (2013.01); *C12P 7/18* (2013.01); *C12P 7/40* (2013.01); *C12P 7/42* (2013.01); *C12P 17/02* (2013.01); *Y02E 50/30* (2013.01); *Y02P 20/582* (2015.11)

(56) References Cited

U.S. PATENT DOCUMENTS

| | | | |
|---|---|---|---|
| 3,847,748 A | | 11/1974 | Gibson et al. |
| 3,910,826 A | | 10/1975 | Kataoka |
| 4,100,730 A | * | 7/1978 | Pradt ............... C02F 11/08 210/761 |
| 4,594,324 A | * | 6/1986 | Dalton ............... C12P 7/02 435/122 |
| 4,847,203 A | | 7/1989 | Smart |
| 4,906,578 A | | 3/1990 | Suzuki et al. |
| 5,021,069 A | * | 6/1991 | Whellock ............ C12P 19/06 423/DIG. 17 |
| 5,503,748 A | | 4/1996 | Merchuk et al. |
| 6,492,135 B1 | | 12/2002 | Larsen |
| 6,689,601 B2 | | 2/2004 | Koffas et al. |
| 6,818,424 B2 | | 11/2004 | DiCosimo et al. |
| 7,098,005 B2 | | 8/2006 | Dicosimo et al. |
| 7,579,163 B2 | * | 8/2009 | Eriksen ............... A23J 1/005 435/252.1 |
| 7,799,550 B2 | | 9/2010 | Moen et al. |
| 7,947,483 B2 | | 5/2011 | Burgard et al. |
| 8,129,155 B2 | | 3/2012 | Trawick et al. |
| 8,268,607 B2 | | 9/2012 | Burgard et al. |
| 8,354,063 B2 | | 1/2013 | Hottoyy et al. |
| 8,592,198 B2 | | 11/2013 | Moen et al. |
| 8,648,209 B1 | | 2/2014 | Lastella |
| 8,795,955 B2 | | 8/2014 | Kinsho et al. |
| 8,993,285 B2 | | 3/2015 | Burgard |
| 2001/0055237 A1 | | 12/2001 | Kubera et al. |
| 2002/0168733 A1 | | 11/2002 | Clark et al. |
| 2002/0192809 A1 | | 12/2002 | Lanting et al. |
| 2007/0003602 A1 | | 1/2007 | Johannessen et al. |
| 2009/0027997 A1 | | 1/2009 | Meier |
| 2010/0035343 A1 | | 2/2010 | Cheng et al. |
| 2011/0107664 A1 | | 5/2011 | Rancis et al. |
| 2011/0244543 A1 | | 10/2011 | Larsen |
| 2011/0265474 A1 | | 11/2011 | Schubert |
| 2011/0283618 A1 | | 11/2011 | Martin et al. |

FOREIGN PATENT DOCUMENTS

| | | |
|---|---|---|
| CN | 201506790 U | 6/2010 |
| CN | 102112595 A | 6/2011 |
| CN | 202379992 U | 8/2012 |
| EP | 0 111 253 A2 | 6/1984 |
| EP | 0 185 407 B1 | 1/1990 |
| EP | 0 418 187 B1 | 12/1994 |
| EP | 1 265 982 B1 | 9/2004 |
| EP | 1 497 409 B1 | 5/2006 |
| EP | 1 183 326 B1 | 3/2007 |
| EP | 1419 234 B1 | 3/2011 |
| EP | 2 427 200 B1 | 4/2014 |
| GB | 1 417 486 A | 12/1975 |
| JP | 50-51972 A | 5/1975 |
| JP | 53-118581 A | 10/1978 |
| JP | 60-075274 A | 4/1985 |
| JP | 63-283570 A | 11/1988 |
| JP | 3-160983 A | 7/1991 |
| JP | 2003-88355 A | 3/2003 |
| JP | 2012-115232 A | 6/2012 |
| KR | 10-2012-0052438 A | 5/2012 |
| RU | 2 021 347 C1 | 10/1994 |
| WO | 01/60974 A2 | 8/2001 |
| WO | 03/016460 A1 | 2/2003 |
| WO | 03/089625 A2 | 10/2003 |
| WO | 2005/087942 A1 | 9/2005 |
| WO | 2010/128312 A2 | 11/2010 |
| WO | 2011/088206 A1 | 7/2011 |
| WO | 2011/159682 A1 | 12/2011 |
| WO | 2012/053905 A1 | 4/2012 |

OTHER PUBLICATIONS

Jiang et al., "Microbiol production of short chain diols," *Microbiol Cell Factories* 13:165 (17 pages) (2014).

Yim et al., "Metabolic engineering of *Escherichia coli* for direct production of 1,4-butanediol," *Nature Chemical Biology* 7:445-452 (2011).

* cited by examiner

C₁ SUBSTRATE-FED FERMENTATION SYSTEMS AND METHODS FOR PRODUCING C₄ COMPOUNDS

BACKGROUND

Technical Field

This invention is generally related to vessels, systems and processes useful in fermentation and, in particular, fermentation systems using a gaseous substrate.

Description of the Related Art

With the ever increasing depletion of fossil fuel deposits, the increasing production of greenhouse gases and recent concerns about climate change, substituting biofuels (e.g., ethanol, biodiesel) for fossil fuels has become an industrial focus. But, biofuels generated to date have their own difficulties and concerns. First generation biofuels are derived from plants (e.g., starch; cane sugar; and corn, rapeseed, soybean, palm, and other vegetable oils), but these fuel crops compete with crops grown for human and animal consumption. The amount of globally available farm land is insufficient to satisfy the increasing needs for both food and fuel. To reduce the demand placed upon food producers for biofuel compatible grains, second generation biofuels using alternative biological material such as cellulose or algae are under development. But, technical difficulties in production, along with the high cost of production, have not made second generation biofuels any more cost-effective or accessible.

Third or next generation biofuels are made using alternative, non-food based, carbon feedstocks. As part of this effort, the use of alternative, non-biological based, feedstocks in the production of higher hydrocarbon compounds including fuels, lubricants, and plastics is gaining ever-increasing momentum. Such feedstocks may include one or more carbon containing compounds or mixtures of carbon containing and non-carbon containing compounds that include, among others, methane and syngas. Methane, for example, is a relatively abundant, naturally occurring and found in many locations throughout the world. Methane is also produced during many biological decay processes, and thus may be captured from waste treatment and landfill facilities. For its relative abundance, methane is a potent greenhouse gas, having 23× the relative greenhouse gas contribution of $CO_2$. Historically, methane has been viewed as a somewhat valuable byproduct that is difficult to convert to higher value products or to transport to the marketplace from remote or stranded locations such as remote gas fields or off-shore production platforms. Methane from such sources, as well as the methane produced by biological decomposition processes occurring at sewage treatment facilities and landfills, is primarily either vented or flared. The ability to economically and efficiently convert methane and similar carbon containing gases to one or more higher value $C_2$ or higher hydrocarbons would permit producers to take advantage of a relatively abundant, non-biologically produced, feedstock while at the same time, providing a significant environmental benefit.

The recent rise in domestic production of methane (from 48 billion cubic feet equivalent per day in 2006 to 65 billion cubic feet equivalent per day in 2012) has driven the cost of natural gas to record lows (from about $14.00/MMBTU in 2006 to about $2.50/MMBTU in 2012). Domestic natural gas is primarily produced by hydraulic fracturing ("fracking"), but methane can also be obtained from other sources, such as landfills and sewage. But, methane's volatility makes the transport and/or direct usage of methane as a fuel problematic.

For these reasons, a strong incentive exists to convert the methane to one or more liquid products, for example motor fuels, to permit easier transport to the point of use or sale. Two main approaches are currently being pursued: liquefaction leading to liquefied natural gas (LNG) and chemical conversion to convert gas-to-liquid (GTL) (Patel, 2005, 7th World Congress of Chemical Engineering, Glasgow, Scotland, UK). The Fischer Tropsch (F-T) process is currently the most prevalent approach for converting large quantities of methane to higher-order hydrocarbons (Patel, 2005). Note that the F-T process takes syngas as an input which is produced from natural gas by steam reforming (syngas can also be sourced from coal gasification, by high temperature reaction with water and oxygen). The F-T process yields petroleum products consistent with today's fuel supply, but suffers from a number of drawbacks, including low yields, poor selectivity (making downstream utilization complex), and requires significant capital expenditure and scale to achieve economical production (Spath and Dayton, December 2003 NREL1TP-510-34929). The massive scale required for an F-T plant (generally in excess of two billion dollars in capital cost [Patel, 2005]) also represents a significant limitation due to the large amount of methane feedstock required to offset the enormous capital cost of the F-T process. As methane transportation is prohibitively expensive in most cases, such a plant must be co-located with a steady, reliable, and cost efficient source of methane, usually in the form of a significant methane reservoir or a methane pipeline. An additional cost and scaling factor is the economics of gas-scrubbing technologies (Spath and Dayton, 2003), since F-T catalysts are quite sensitive to common contaminants found in natural gas that pass unaffected through the syngas conversion process.

The requirements for ready access to large volumes of a relatively clean methane containing gas, combined with a massive capital investment, currently limit natural gas based F-T plants to successful and economically viable operation in only a few locations world-wide (Spath and Dayton, 2003). The high minimum processing requirement for a gas-to-liquids process or liquefied natural gas plant, combined with the high cost of transport, result in smaller methane sources remaining as 'stranded' gas deposits. Such stranded gas can include, but is not limited to, natural gas produced at off-shore oil wells, or methane off-gas from landfills. Due to the current absence of efficient small-scale conversion technologies, such stranded gas sources are typically vented to atmosphere or flared, as methane accumulation presents a significant safety risk. Gas-to-liquids facilities using the Fischer-Tropsh process have been in operation semi-continuously since 1938. Several companies are currently investigating introduction of new plants given the current availability and price of methane discussed above. However, despite significant research and development over the last 70+ years, the limitations of Fischer-Tropsch technology prevent broad adoption of commercial gas-to-liquids processes.

In view of the above limitations, biological fermentation using $C_1$ substrates as a carbon source presents an attractive solution to both the current competition between food sources and fermentation for chemicals/fuels, as well as the lack of good options for utilization of natural gas. However, fermentation of gaseous substrates such as methane, CO, or $CO_2$ presents significant challenges due to the requirement that the carbon substrate must be transferred from the gas phase to an aqueous phase to allow for uptake and metabolism by the $C_1$ metabolizing non-photosynthetic microorganisms in culture. Simultaneously, other gasses such as $O_2$ or $H_2$ may also be required to be transferred from the gas phase to allow cellular metabolism to progress (aerobic or anaerobic metabolism, respectively). Waste products (such as $CO_2$ in the case of aerobic metabolism) must be removed rapidly from the reactor to allow for efficient microbial growth. Further, the heat generation from metabolism of $C_1$ substrates is significant and the system must be cooled continuously to maintain optimal conditions for microbial growth.

Convective mass transfer from the liquid phase to the vapor phase can be described with a mass transfer coefficient. The flux is equal to the product of the mass transfer coefficient, the surface area, and the concentration difference (Flux=k A $\Delta$C).

The mass transfer coefficient is influenced by a variety of factors including the size of the molecule to be transferred, its solubility in the aqueous phase, and the size of the boundary layer between the phases (typically controlled in fermentation systems by mixing speed and turbulence). The surface area between the gas and liquid phases in most fermentation systems is primarily limited by the bubble size of the input gas. Bubble size can be controlled by introducing the gas through small pores, as well as increasing shear forces to break apart bubbles and prevent coalescence. The concentration difference can be the concentration difference across the gas phase boundary layer, the concentration difference across the liquid phase boundary layer, the concentration difference between the bulk vapor and the vapor which would be in equilibrium with the bulk liquid, or the concentration difference between the bulk liquid and the liquid which would be in equilibrium with the bulk vapor. In most fermentation systems, the concentration difference is controlled by the pressure of the gas phase.

Conventional fermentation systems (bioreactors) achieve gas mixing by one of two methods: stirring or airlift. Stirred fermentors achieve mixing by means of stirring blades generally placed centrally in a single large fermentor. The stirrer blades generate turbulence and shear in the liquid while gas bubbles are introduced at the bottom of the fermentor, thus impeding the progress of the bubbles as they travel up the fermentor and shearing the gas bubbles to reduce the tendency of the bubbles to coalesce within the fermentor. The advantage of this type of fermentor is the fast, relatively homogeneous mixing and gas bubble dispersion that is possible due to the high speed of the mixing blades. However, this type of fermentor can be difficult to scale-up, as the energy requirements to obtain the same rate of mixing and mass transport can be prohibitive as the volume increases. Further, the vigorous mixing implies a significant heating of the fermentation liquid, and the use of a single large fermentor limits the surface area available for heat exchange cooling.

Airlift fermentors avoid mechanical stirrers by incorporating a flow path for the liquid. Airlift fermentors have a downflow and an upflow section which are interconnected at both ends; these sections can either be separate units (referred to as a loop fermentor), or concentric (airlift fermentor). In either case, gasses are supplied at the bottom of the upflow section through a bubble-generating apparatus. The bubbles mix with the liquid, reducing the density of the liquid and causing the gas-liquid mixture to rise through the upflow section. The rising mixture displaces liquid at the top of the reactor, which travels down the downflow section to replace the liquid at the bottom, establishing a circular flow in the fermentor. In order to obtain a long residence time for the gas bubbles in the liquid, airlift fermentors are generally tall and have a limited transverse cross-sectional area. This implies that the gas must be supplied at a relatively high pressure to overcome hydrostatic pressure formed by the column of liquid present in the fermentor. In addition, the bubble size increases significantly throughout the fermentor as the pressure decreases with height. The increasing bubble diameter proportionately reduces the rate of mass transfer between the gas bubbles and the liquid phase by reducing the ratio of gas bubble volume (proportionate to the cube of the gas bubble radius) to gas bubble area (proportionate to the square of the gas bubble area) through which mass transfer may occur. Flow rates and shear forces in airlift fermentors are significantly lower than in stirred tank fermentors, which also tend to increase bubble coalescence and reduce the efficiency of cooling the fermentor. Finally, separation of the unused and waste gases from the mixture exiting the upflow portion of the fermentor prior to the return of the liquid to the downflow section can be challenging.

BRIEF SUMMARY

In one aspect, the present disclosure provides a method and apparatus for efficient mass transfer of gaseous substrates for microbial fermentation. Additionally, this disclosure provides a method for fermenting gaseous carbon-containing feedstocks using a culture primarily comprising a $C_1$ metabolizing non-photosynthetic microorganism. In yet another aspect, this disclosure provides a scalable fermentor design for allowing high flux gas-phase to liquid-phase mass transfer in addition to efficient heat exchange and waste gas removal. Systems and methods for fermentation that overcome disadvantages known in the art and provide the public with new methods for the optimal production of a variety of products are provided.

Such fermentation systems may employ one or more species of microorganism that are preferentially capable of metabolizing $C_1$ compounds. Such microorganisms include prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas,* or *Pseudomonas*. In some instances, the $C_1$ metabolizing microorganisms may include methanotrophs, methylotrophs or combinations thereof. Preferred methanotrophs include *Methylomonas, Methylobacter, Methylococcus, Methylosinus, Methylocystis, Methylomicrobium, Methanomonas,* or combinations thereof. Exemplary methanotrophs include *Methylomonas* sp. 16a (ATCC PTA 2402), *Methylosinus trichosporium* (NRRL B-11,196), *Methylosinus sporium* (NRRL B-11, 197), *Methylocystis parvus* (NRRL B-11, 198), *Methylomonas methanica* (NRRL B-5 11,199), *Methylomonas albus* (NRRL B-11,200), *Methylobacter capsulatus* (NRRL B-11,201), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylosinus trichosporium* OB3b, *Methylococcus capsulatus* Bath, *Methylomonas* sp. 16a, *Methylomicrobium alcaliphilum* 20Z, or high growth variants thereof. Preferred methylotrophs include *Methylobacterium extorquens, Methylobacterium radiotolerans, Methylobacterium populi, Methylobacterium chloromethanicum, Methylobacterium nodulans,* or combinations thereof.

Microorganisms capable of metabolizing $C_1$ compounds found in syngas include, but are not limited to *Clostridium, Moorella, Pyrococcus, Eubacterium, Desulfobacterium, Carboxydothermus, Acetogenium, Acetobacterium, Acetoanaerobium, Butyribaceterium, Peptostreptococcus*, or combinations thereof. Exemplary methylotrophs include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or combinations thereof. In some instances, $C_1$ metabolizing microorganisms are eukaryotes such as yeast, including *Candida, Yarrowia, Hansenula, Pichia, Torulopsis*, or *Rhodotorula*.

In other instances, the $C_1$ metabolizing non-photosynthetic microorganism is an obligate $C_1$ metabolizing non-photosynthetic microorganism, such as an obligate methanotroph an obligate methylotroph, or combinations thereof. In some instances, the $C_1$ metabolizing non-photosynthetic microorganism is a recombinant microorganism comprising a heterologous polynucleotide encoding a fatty acid producing enzyme, a formaldehyde assimilation enzyme, or combinations thereof.

BRIEF DESCRIPTION OF THE DRAWINGS

In the drawings, the sizes and relative positions of elements in the drawings are not necessarily drawn to scale. For example, the various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

DETAILED DESCRIPTION

Figure 1:
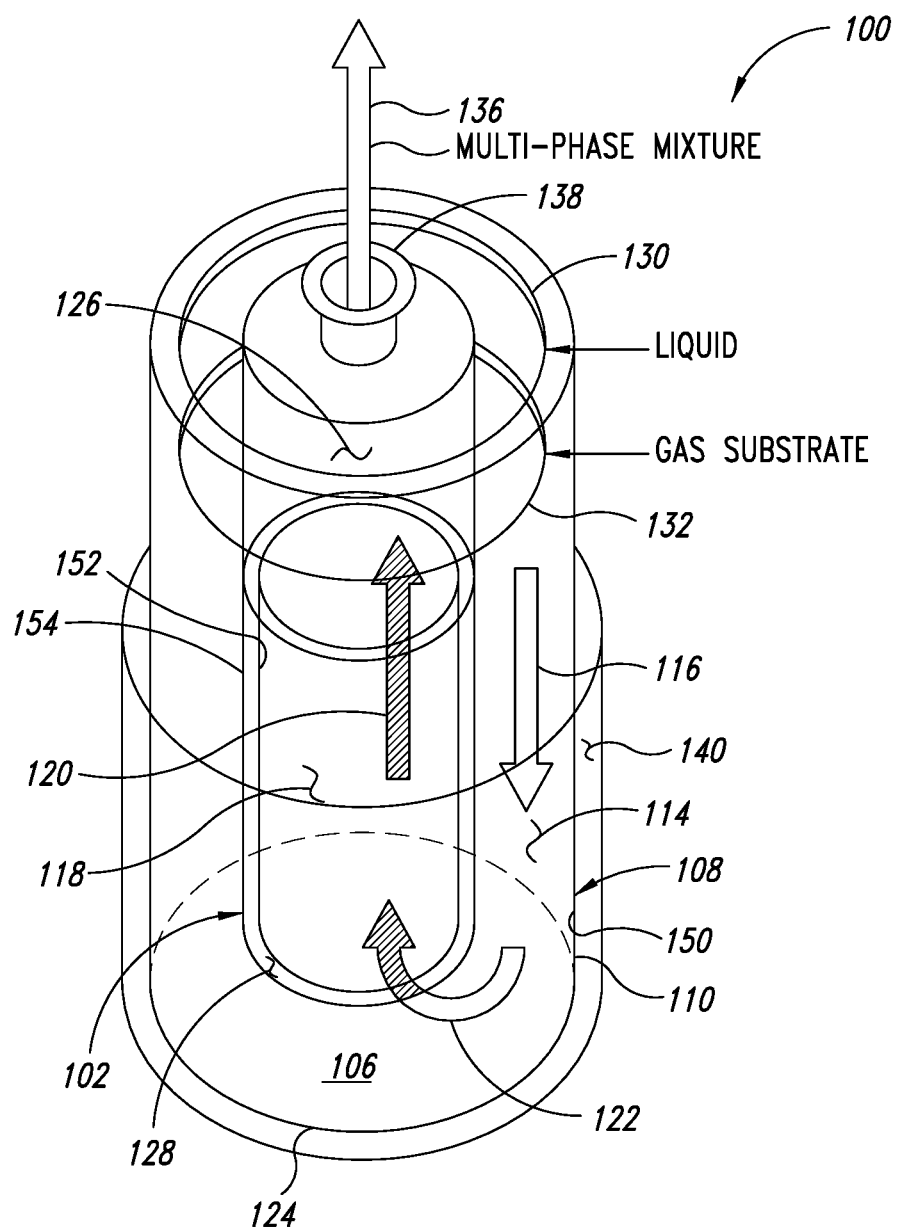
FIG. 1 shows a perspective view of an example fermentor vessel including a number of hollow fluid conduits disposed within the vessel to create a number of downward flow paths between each of the number of hollow fluid conduits and the surrounding vessel and a number of upward flow paths within each of the number of hollow fluid conduits; the downward and upward flowpaths are fluidly coupled such that at least a portion of the flow in the downward flowpath enters the hollow fluid conduit to provide at least a portion of the flow in the upward flow path, according to one or more illustrated embodiments.

In the following description, certain specific details are set forth in order to provide a thorough understanding of various embodiments. However, one skilled in the art will understand that the invention may be practiced without these details. In other instances, structures, standard vessel design details, detailed design parameters of available components such as liquid or gas distributors, pumps, turbines, and similar, details concerning the design and construction of American Society of Mechanical Engineers (ASME) pressure vessels, control system theory, specific steps in one or more fermentation processes, and the like have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or"

is generally employed in its sense including "and/or" unless the content clearly dictates otherwise.

Fermentors are generally defined as any vessel in which a fermentation process is carried out. Given the vast number of fermentation processes and the wide variety of fermentable substrates, fermentors can range simple continuous stirred tank reactors found in the alcoholic beverage industry to highly complex, specialized vessels having gas distribution and internal structures tailored to a particular substrate and/or a particular biological species. Fermentors useful in converting carbon containing gases such as methane and syngas (a mixture of CO and $H_2$) to longer chain gaseous and liquid hydrocarbons generally disperse a gas substrate containing the $C_1$ carbon compound within a liquid media containing one or more nutrients to provide a multi-phase mixture. This multi-phase mixture is fed to one or more microbiological colonies that convert a portion of the $C_1$ carbon compound(s) in the gas substrate to more preferred, longer chain, $C_2$ or higher compounds. The substrate composition, nutrients, and microbiological organisms comprising the colony (i.e., the biomass within the fermentor) can be variously adjusted or tailored to provide a desired final matrix of $C_2$ or higher compounds which may be present as a liquid, gas, or intracellular material.

From a mass transfer perspective, gas substrate fermentors present a unique challenge in that the substrate is trapped within a gas bubble and in order for microbiological uptake of the substrate to occur, the gas substrate must first pass from the gas bubble to the microbiological organisms either directly or indirectly via dissolution in the liquid media. Such fermentation processes are thus frequently limited by the ability of the system to facilitate and/or sustain a desirably high level of mass transfer of the substrate from the gas bubbles to the microbiological organisms within the fermentor. At the least, the rate of mass transfer from the gas bubble to either the surrounding liquid media or to a microbiological organisms is a function of the gas pressure within the gas bubble, the volume to surface area ratio of the gas bubble, and the contact time of the gas bubble with the surrounding liquid or microbiological organisms. Increasing the pressure within the gas bubble or increasing the contact time of the gas bubble with the surrounding liquid or microbiological organisms results in a higher effective mass transfer rate between the substrate and the microbiological organisms. Decreasing the volume to surface area ratio of the gas bubble (i.e., reducing the diameter of the gas bubbles) results in a higher effective mass transfer rate between the gas bubble and the surrounding liquid. An ideal fermentor would therefore have a large number of relatively small diameter gas bubbles at a relatively high pressure that are held in close or intimate contact with the surrounding liquid or microbiological organisms for an extended period of time.

Disclosed herein are a number of fermentation systems, methods, and apparatuses that are capable of providing relatively small diameter, relatively high pressure gas bubbles. Disclosed herein are a number of fermentation systems, methods, and apparatuses capable of providing an extended contact time with the surrounding liquid and/or biological organism(s). Such fermentation systems, methods, and apparatuses can advantageously provide a highly efficient gas substrate fermentation system that has been found particularly useful in converting $C_1$ compounds to more preferred gaseous, liquid, and intra-cellular $C_2$ and higher compounds.

As used herein, the terms "$C_1$ substrate" or "$C_1$ compound" refers to any carbon containing molecule or composition that lacks a carbon-carbon bond. Sample molecules or compositions include methane, methanol, formaldehyde, formic acid or a salt thereof, carbon monoxide, carbon dioxide, syngas, methylamines (e.g., monomethylamine, dimethylamine, trimethylamine), methylthiols, or methylhalogens.

As used herein, the terms "$C_1$ metabolizing microorganism" or "$C_1$ metabolizing non-photosynthetic microorganism" refers to any microorganism having the ability to use a single carbon ($C_1$) substrate as a source of energy or as its sole source of energy and biomass, and may or may not use other carbon substrates (such as sugars and complex carbohydrates) for energy and biomass. For example, a $C_1$ metabolizing microorganism may oxidize a $C_1$ substrate, such as methane or methanol. $C_1$ metabolizing microorganisms include bacteria (such as Methanotrophs and Methylotrophs) and yeast. In at least some instances, a $C_1$ metabolizing microorganism does not include a photosynthetic microorganism, such as algae. In certain embodiments, the $C_1$ metabolizing microorganism will be an "obligate $C_1$ metabolizing microorganism," meaning its sole source of energy comprises $C_1$ substrates and nothing else.

As used herein, the term "methylotrophic bacteria" refers to any bacteria capable of oxidizing organic compounds that do not contain carbon-carbon bonds. In certain embodiments, a methylotrophic bacterium may be a methanotroph. For example, "methanotrophic bacteria" refers to any methylotrophic bacteria that have the ability to oxidize methane as its primary source of carbon and energy. Exemplary methanotrophic bacteria include *Methylomonas, Methylobacter, Methylococcus, Methylosinus, Methylocystis, Methylomicrobium*, or *Methanomonas*. In certain other embodiments, the methylotrophic bacterium is an "obligate methylotrophic bacterium," which refers to bacteria that are limited to the use of $C_1$ substrates for the generation of energy.

As used herein, the term "CO utilizing bacterium" refers to a bacterium that naturally possesses the ability to oxidize carbon monoxide (CO) as a source of carbon and energy. Carbon monoxide may be utilized from "synthesis gas" or "syngas", a mixture of carbon monoxide and hydrogen produced by gasification of any organic feedstock, such as coal, coal oil, natural gas, biomass, and waste organic matter. Carbon monoxide utilizing bacterium does not include bacteria that must be genetically modified for growth on carbon monoxide as its carbon source.

As used herein, the term "syngas" refers to a mixture including at least carbon monoxide (CO) and hydrogen ($H_2$). In at least some instances, syngas may also include $CO_2$, methane, and other gases in smaller quantities relative to CO and $H_2$. Syngas may be prepared using any available process, including but not limited to, a water gas shift or coal gasification process.

As used herein, the term "growth" is defined as any increase in cell mass. This may occur through cell division (replication) and the formation of new cells during "balanced growth," or during "unbalanced growth" when cellular mass increases due to the accumulation of one or more intracellular or intercellular polymers, such as certain lipids. In the latter case, growth may be manifest as an increase in cell size due to the accumulation of a biopolymer within the cell. During "balanced cell growth," all of the feedstocks (electron donors and electron acceptors) and all of the nutrients are present in the ratios required to make all of the macromolecular components of a cell. That is, no feedstock or nutrient limits the synthesis of proteins, complex carbohydrate polymers, fats, or nucleic acids. In contrast, during "unbalanced cell growth," a feedstock or nutrient needed to make one or more of a cell's macromolecules is not present in an amount or ratio required for balanced growth. Accordingly, this feedstock or nutrient becomes limiting and is referred to as a "limiting nutrient."

Some cells may still achieve net growth under unbalanced conditions, but the growth is unbalanced and polymers that can be synthesized in the absence of the limiting feedstock or nutrient will accumulate. These polymers include lipids or intracellular storage products, such as the polyhydroxyalkanoates (PHAs), including polyhydroxybutyrate (PHB), polyhydroxyvalerate (PHV), and polyhydroxyhexanoate (PHHx)-glycogen, or secreted materials, such as extracellular polysaccharide. Such oil compositions are useful in the production of bioplastics.

Sample balanced and unbalanced growth conditions may differ in the nitrogen content in the media. For example, nitrogen constitutes about 12% of dry cell weight, which means that 12 mg/L nitrogen must be supplied (along with a feedstock and other nutrients in the required stoichiometric ratios) to grow 100 mg/L dry cell weight. If other feedstock and nutrients are available in the quantities needed to produce 100 mg/L of dry cell weight, but less than 12 mg/L nitrogen is provided, then unbalanced cell growth may occur, with accumulation of polymers that do not contain nitrogen. If nitrogen is subsequently provided, the stored polymer may serve as feedstock for the cell, allowing balanced growth, with replication and production of new cells.

As used herein, the term "growth cycle" as applied to a cell or microorganism refers to the metabolic cycle through which a cell or microorganism moves in culture conditions. For example, the cycle may include various stages, such as a lag phase, an exponential phase, the end of exponential phase, and a stationary phase.

As used herein, the term "exponential growth", "exponential phase growth", "log phase" or "log phase growth" refer to the rate at which microorganisms are growing and dividing. For example, during log phase, microorganisms are growing at their maximal rate given their genetic potential, the nature of the medium, and the conditions under which they are grown. Microorganism rate of growth is constant during exponential phase and the microorganism divides and doubles in number at regular intervals. Cells that are "actively growing" are those that are growing in log phase. In contrast, "stationary phase" refers to the point in the growth cycle during which cell growth of a culture slows or even ceases.

As used herein, the term "growth-altering environment" refers to energy, chemicals, or living things that have the capacity to either inhibit cell growth or kill cells. Inhibitory agents may include mutagens, drugs, antibiotics, UV light, extreme temperature, pH, metabolic byproducts, organic chemicals, inorganic chemicals, bacteria, viruses, or the like.

As used herein, the term "high growth variant" refers to a organism, microorganism, bacterium, yeast, or cell capable of growth with a $C_1$ substrate, such as methane or methanol, as the sole carbon and energy source and which possesses an exponential phase growth rate that is faster than the parent, reference or wild-type organism, microorganism, bacterium, yeast, or cell—that is, the high growth variant has a faster doubling time and consequently a high rate of growth and yield of cell mass per gram of $C_1$ substrate metabolized as compared to a parent cell (see, e.g., U.S. Pat. No. 6,689, 601).

As used herein, the term "biofuel" refers to a fuel at least partially derived from "biomass."

As used herein, the term "biomass" refers to a renewable resource having a biological origin.

As used herein, the term "biorefinery" refers to a facility that integrates biomass conversion processes and equipment to produce fuels from biomass.

As used herein, the term "refinery" refers to an oil refinery, or aspects thereof, at which oil compositions (e.g., biomass, biofuel, or fossil fuels such as crude oil, coal or natural gas) may be processed. Sample processes carried out at such refineries include cracking, transesterification, reforming, distilling, hydroprocessing, isomerization, or any combination thereof.

As used herein, the terms "recombinant" or "non-natural" refers to an organism microorganism, cell, nucleic acid molecule, or vector that has at least one genetic alternation or has been modified by the introduction of a heterologous nucleic acid molecule, or refers to a cell that has been altered such that the expression of an endogenous nucleic acid molecule or gene can be controlled. Recombinant also refers to a cell that is derived from a cell having one or more such modifications. For example, recombinant cells may express genes or other nucleic acid molecules that are not found in identical form within the native cell (i.e., unmodified or wild type cell), or may provide an altered expression pattern of endogenous genes, such genes that may otherwise be over-expressed, under-expressed, minimally expressed, or not expressed at all. In another example, genetic modifications to nucleic acid molecules encoding enzymes or functional fragments thereof can provide biochemical reaction(s) or metabolic pathway capabilities to a recombinant microorganism or cell that is new or altered from its naturally occurring state.

As used herein, the term "heterologous" nucleic acid molecule, construct or sequence refers to a nucleic acid molecule or portion of a nucleic acid molecule sequence that is not native to a cell in which it is expressed or is a nucleic acid molecule with an altered expression as compared to the native expression levels in similar conditions. For example, a heterologous control sequence (e.g., promoter, enhancer) may be used to regulate expression of a gene or a nucleic acid molecule in a way that is different than the gene or a nucleic acid molecule is normally expressed in nature or culture. Generally, heterologous nucleic acid molecules are not endogenous to the cell or part of the genome in which they are present, and have been added to the cell by conjugation, transformation, transfection, electroporation, or the like.

The systems for fermentation of the instant disclosure may include separate units (e.g., processing units or systems that are disposed in close proximity or adjacent to each other, or not), integrated units, or the system itself may be interconnected and integrated. The systems of this disclosure may use at least one gas phase feedstock, including one or more $C_1$ compounds, oxygen, and/or hydrogen. In certain embodiments, the fermentation system uses a $C_1$ metabolizing microorganism (e.g., a methanotroph such as *Methylosinus trichosporium* OB3b, *Methylococcus capsulatus* Bath, *Methylomonas* sp. 16a, *Methylomicrobium alcaliphilum* 20Z, or high growth variants or combinations thereof) as the primary microorganism in the fermentation culture.

A variety of culture methodologies may be used for the microorganism, bacteria and yeast described herein. For example, $C_1$ metabolizing microorganisms, such as methanotroph or methylotroph bacteria, may be grown by batch culture and continuous culture methodologies. Generally cells in log phase are often responsible for the bulk production of a product or intermediate of interest in some systems, whereas stationary or post-exponential phase production can be obtained in other systems.

A classical batch culturing method is a closed system in which the media composition is set when the culture is started and is not altered during the culture process. That is, media is inoculated at the beginning of the culturing process with one or more microorganisms of choice and then are allowed to grow without adding anything to the system. As used herein, a "batch" culture is in reference to not changing the amount of a particular carbon source initially added, whereas control of factors such as pH and oxygen concentration can be monitored and altered during the culture. In batch systems, metabolite and biomass compositions of the system change constantly up to the time the culture is terminated. Within batch cultures, cells (e.g., bacteria such as methylotrophs) will generally move from a static lag phase to a high growth logarithmic phase to a stationary phase where growth rate is reduced or stopped (and will eventually lead to cell death if conditions do change).

A fed-batch system is a variation on the standard batch system in which a carbon substrate of interest is added in increments as the culture progresses. Fed-batch systems are useful when cell metabolism is likely to be inhibited by catabolite repression and when it is desirable to have limited amounts of substrate in the media. Since it is difficult to measure actual substrate concentration in fed-batch systems, an estimate is made based on changes of measurable factors such as pH, dissolved oxygen, and the partial pressure of waste gases. Batch and fed-batch culturing methods are common and known in the art (see, e.g., Thomas D. Brock, Biotechnology: A Textbook of Industrial Microbiology, 2nd Ed. (1989) Sinauer Associates, Inc., Sunderland, Mass.; Deshpande, 1992, Appl. Biochem. Biotechnol. 36:227).

Continuous cultures are "open" systems in the sense that defined culture media is continuously added to a bioreactor while an equal amount of used ("conditioned") media is removed simultaneously for processing. Continuous cultures generally maintain the cells at a constant high, liquid phase density where cells are primarily in logarithmic growth phase. Alternatively, continuous culture may be practiced with immobilized cells (e.g., biofilm) where carbon and nutrients are continuously added and valuable products, by-products, and waste products are continuously removed from the cell mass. Cell immobilization may be achieved with a wide range of solid supports composed of natural materials, synthetic materials, or a combination thereof.

Continuous or semi-continuous culture allows for the modulation of one or more factors that affect cell growth or end product concentration. For example, one method may maintain a limited nutrient at a fixed rate (e.g., carbon source, nitrogen) and allow all other parameters to change over time. In other embodiments, several factors affecting growth may be continuously altered while cell concentration, as measured by media turbidity, is kept constant. The goal of a continuous culture system is to maintain steady state growth conditions while balancing cell loss due to media being drawn off against the cell growth rate. Methods of modulating nutrients and growth factors for continuous culture processes and techniques for maximizing the rate of product formation are well known in the art (see Brock, 1992).

In certain embodiments, culture media includes a carbon substrate as a source of energy for a $C_1$ metabolizing microorganism. Suitable substrates include $C_1$ substrates, such as methane, methanol, formaldehyde, formic acid (formate), carbon monoxide, carbon dioxide, methylated amines (methylamine, dimethylamine, trimethylamine, etc.), methylated thiols, or methyl halogens (bromomethane, chloromethane, iodomethane, dichloromethane, etc.). In certain embodiments, culture media may comprise a single $C_1$ substrate as the sole carbon source for a $C_1$ metabolizing microorganism, or may comprise a mixture of two or more $C_1$ substrates (mixed $C_1$ substrate composition) as multiple carbon sources for a $C_1$ metabolizing microorganism.

Additionally, some $C_1$ metabolizing organisms are known to utilize non-$C_1$ substrates, such as sugar, glucosamine or a variety of amino acids for metabolic activity. For example, some Candida species can metabolize alanine or oleic acid (Sulter et al., Arch. Microbiol. 153:485-489, 1990). Methylobacterium extorquens AM1 is capable of growth on a limited number of $C_2$, $C_3$, and $C_4$ substrates (Van Dien et al., Microbiol. 149:601-609, 2003). Alternatively, a $C_1$ metabolizing microorganism may be a recombinant variant having the ability to utilize alternative carbon substrates. Hence, it is contemplated that a carbon source in culture media may comprise a mixture of carbon substrates, with single and multi-carbon compounds, depending on the $C_1$ metabolizing microorganism selected.

In certain embodiments, the instant disclosure provides a method for making fuel, comprising converting biomass from a culture primarily comprising a $C_1$ metabolizing non-photosynthetic microorganism into an oil composition and refining the oil composition into a fuel. In certain embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. In further embodiments, the oil composition is derived or extracted from cell membrane of the $C_1$ metabolizing non-photosynthetic microorganism, such as a methylotroph or methanotroph.

In certain embodiments, the instant disclosure provides a method for making fuel by refining an oil composition in a refining unit to produce fuel, wherein the oil composition is derived from a $C_1$ metabolizing non-photosynthetic microorganism, such as a methylotroph or methanotroph. In further embodiments, the method further comprises use of a processing unit for extracting the oil composition from the $C_1$ metabolizing non-photosynthetic microorganism. In still further embodiments, the method comprises (a) culturing $C_1$ metabolizing bacteria in the presence of a feedstock comprising a $C_1$ substrate in a controlled culturing unit, wherein the cultured bacteria produces an oil composition; (b) extracting the oil composition from the cultured bacteria in a processing unit; and (c) refining the extracted oil composition in a refining unit to produce fuel. In certain embodiments, the feedstock $C_1$ substrate is methane, methanol, formaldehyde, formic acid, carbon monoxide, carbon dioxide, a methylamine, a methylthiol, or a methylhalogen.

In certain embodiments, the instant disclosure provides a method for making natural products, such as ethanol, acetate, butanol, single-cell protein, sugars, or other metabolites or cellular products wherein the natural product is derived from a $C_1$ metabolizing non-photosynthetic microorganism, such as a methylotroph or methanotroph.

In further embodiments, the method further comprises use of a processing unit for extracting the natural product from the $C_1$ metabolizing non-photosynthetic microorganism.

In still further embodiments, the method comprises (a) culturing $C_1$ metabolizing bacteria in the presence of a feedstock comprising a $C_1$ substrate in a controlled culturing unit, wherein the cultured bacteria produce a natural product; (b) extracting the natural product from the cultured bacteria in a processing unit; and (c) refining the natural product to produce a commercial product. In certain embodiments, the feedstock $C_1$ substrate is methane, methanol, formaldehyde, formic acid, carbon monoxide, carbon dioxide, a methylamine, a methylthiol, or a methylhalogen.

In certain embodiments, the instant disclosure provides a method for making natural or non-natural products, such as acetate, ethanol, ethylene glycol, propylene, propylene oxide, 3-hydroxypropionic acid or a salts thereof, crotonic acid or salts thereof, butanol (e.g., isobutanol, n-butanol), 1,3-butanediol, 1,4-butanediol, 2,3-butanediol, isoprene, farnesene, enzymes, or other metabolites or cellular products wherein the product is derived from a genetically engineered $C_1$ metabolizing non-photosynthetic microorganism, such as a methylotroph or methanotroph which has been transformed with a heterologous nucleotide sequence. In further embodiments, the method further comprises use of a processing unit for extracting the product from the genetically engineered $C_1$ metabolizing non-photosynthetic microorganism. In still further embodiments, the method comprises (a) culturing genetically engineered $C_1$ metabolizing bacteria in the presence of a feedstock comprising a $C_1$ substrate in a controlled culturing unit, wherein the cultured bacteria produce a natural product; (b) extracting the natural product from the cultured bacteria in a processing unit; and (c) refining the natural product to produce a commercial product. In certain embodiments, the feedstock $C_1$ substrate is methane, methanol, formaldehyde, formic acid, carbon monoxide, carbon dioxide, a methylamine, a methylthiol, or a methylhalogen.

In certain embodiments, the instant disclosure provides a method for making natural or non-natural products, such as acetate, ethanol, ethylene glycol, propylene, propylene oxide, 3-hydroxypropionic acid or a salts thereof, crotonic acid or salts thereof, butanol (e.g., isobutanol, n-butanol), 1,3-butanediol, 1,4-butanediol, 2,3-butanediol, isoprene, farnesene, enzymes, or other metabolites or cellular products wherein the product is derived from a non-$C_1$ metabolizing microorganism, such as *Escherichia coli, Saccaromyces cerevisiae*, or other common production microorganism. In certain embodiments, the feedstock substrate is glucose, sucrose, glycerol, cellulose or other multicarbon feedstocks.

FIG. 1 shows an example fermentor 100 including a number of hollow fluid conduits 102 (only one shown in FIG. 1 for clarity) disposed within an interior space 106 formed by a vessel 108. The vessel 108 can include one or more walls 110, a bottom 124 and an optional top 126 that partially or completely encloses the hollow fluid conduit 102, the vessel 108, or both. At least a portion of the space existent between the number of hollow fluid conduits 102 and the vessel 108 provides one or more downward flow paths 114 through which a downward flow 116 may occur. At least a portion of the space existent within each of the number of hollow fluid conduits 102 provides one or more upward flow paths 118 through which an upward flow 120 may occur. One or more liquid distributors 130 may be disposed in, on, or about the vessel 108 to introduce one or more liquids to the downward flow path 114. One or more gas distributors 132 may be disposed in, on, or about the vessel 108 to introduce one or more gases or gas substrates to the downward flow path 114. The positioning of the hollow fluid conduit 102 within the vessel 108 advantageously allows for a more accurate and a more consistent scaling than either loop or airlift fermentor designs, since the volume of the fermentor 100 is scaled based upon the radius or cross-sectional profile rather than length.

The addition of one or more substrate gases via the one or more gas distributors 132 in some instances, promotes the formation of finely divided substrate gas bubbles to the liquid within the downward flow path 114. The combination of the liquid and the finely divided, dispersed gas or gas substrate bubbles creates a multi-phase mixture having a generally a downward flow 116 in the downward flow path 114. The downward flow 116 includes a significant number of entrained gas or substrate gas bubbles dispersed within the multi-phase mixture liquid. The difference in density between the gas bubbles and the liquid in the multi-phase mixture causes the gas or gas substrate bubbles to tend to rise upward. However, by maintaining the superficial velocity of the downward flow 116 in the downward flow path 114 at a rate greater than the gas bubble rise rate, gas substrate bubbles present in the multiphase mixture in the downward flow path 114 will travel at a reduced velocity in a generally downward direction. The net velocity of the gas substrate bubbles in the downward flow path 114 is the superficial velocity of the multiphase fluid in the downward flow path 114 minus the rise rate of the gas substrate bubbles. Since the gas substrate bubbles travel through the downward flow path 114 at a velocity less than the comparable rise rate in an airlift fermentor, contact time between the gas substrate bubbles and microbiological organisms existent within the downward flow path 114 is advantageously increased over airlift type fermentors. Although only one liquid distributor 130 and one gas distributor 132 are shown in FIG. 1 for clarity, any number of additional liquid distributors, gas distributors, or combinations thereof may be added at regular or irregular intervals within the downward flow path 114.

The multi-phase mixture in the downward flow path 114 enters 122 the upward flow path 118 via one or more fluid conduits, openings, orifices, apertures, or gaps fluidly connecting or fluidly coupling the number of hollow fluid conduits 102 (i.e., the upward flow path 118) to the interior space 106 of the vessel 108 existent between the vessel wall 110 and the number of hollow fluid conduits 102 (i.e., the downward flow path). In one instance, the multi-phase mixture in the downward flow path 114 can enter the hollow fluid conduit 102 via a gap between the hollow fluid conduit and the bottom 124 of the vessel 108. In at least some instances, the bottom 124 of the vessel 108 can be shaped, formed, or configured to promote the accumulation of biological material (i.e., "biosolids" or "biomass") at a desired location within the vessel 108. For example, the bottom 124 can be conically shaped, dished, or sloped such that biomass falling to the bottom of the fermentor 100 preferentially collects in one or more predetermined locations. In such instances, each of the number of hollow fluid conduits 102 may have different lengths in order to maintain a defined desired or preferred gap or spacing between the inlet of each of the number of hollow fluid conduits 102 and the bottom 124 of the vessel 108.

Having entered the upward flow path 118, the multi-phase mixture creates an upward flow 120 therein. Both the fluid and the gas bubbles in the upward flow path 118 will travel in a generally upward direction. The rise rate of the gas bubbles within the upward flow path 118 is equal to the velocity of the fluid plus the rise rate of the gas bubbles within the fluid. In at least some instances, any number of additional liquid distributors 130, gas distributors 132, or combinations thereof may be added at regular or irregular intervals within the upward flow path 118.

The multi-phase mixture 136 flows from the upward flow path 118 and exits the fermentor 100 via one or more multi-phase mixture discharge connections 138. In at least some instances, one or more multi-phase mixture discharge connections 138 may fluidly coupled to each of the upward flow paths 118 provided by the number of hollow fluid conduits 102. In some instances, the one or more multi-phase mixture discharge connections 138 can include one or more flanged or threaded connections. In some instances, the one or more multi-phase mixture discharge connections 138 can include one or more quick disconnect or similar easily sterilizable fluid couplings or connections.

In some instances, thermal energy (e.g., in the form of sensible heat) may be generated or liberated by the fermentation process or processes occurring within the fermentor 100. Left uncontrolled, sufficient thermal energy can build within the fermentor 100 to adversely affect the growth or metabolism of the microbiological organisms within the fermentor 100. In some instances, uncontrolled thermal energy increases can result in the death of all or a portion of the microbiological organisms within the fermenter. To remove at least a portion of the thermal energy from the fermentor 100, one or more thermal transfer surfaces 128 may be disposed on the interior or exterior of the hollow fluid conduit 102, one or more thermal transfer surfaces 140 may be disposed on the interior or exterior of the vessel 106, or such thermal transfer surfaces 128, 140 may be disposed on any combination of surfaces in fluid and thermal contact with either or both the downward flow path 114 and the upward flow path 118.

The fermentor 100 can include any number of hollow fluid conduits 102 disposed wholly or partially in the interior space 106 formed by a vessel 108. Each of the number of hollow fluid conduits 102 can include any size, shape, or configuration closed fluid channel having a constant or variable cross-sectional profile and a constant or variable wall thickness. Each of the hollow fluid conduits 102 includes at least one opening or inlet that permits the entry of the multi-phase mixture into the upward flow path 118 on the inside of each of the number of hollow fluid conduits 102. Each of the number of hollow fluid conduits 102 includes at least one opening or outlet that permits the exit of the multi-phase mixture 136 from the upward flow path 118. The vessel 108 can have any size, shape, or configuration having one or more walls 110 that form or otherwise define the interior space 106. The interior perimeter formed by the one or more walls 110 provides the transverse cross-sectional profile and the transverse cross-sectional area of the vessel 108. The one or more walls 110 also form the interior perimeter 150 of the vessel 108.

Each of the hollow fluid conduits 102 includes an interior perimeter 152, at least a portion of which is in fluid contact with the upward flow path 118, and an exterior perimeter 154, at least a portion of which is in fluid contact with the downward flow path 114. The downward flow path 114 is bounded by the exterior perimeter 154 of the hollow fluid conduit 102 and the interior perimeter 150 of the vessel 108. The upward flow path 120 is bounded by the interior perimeter 154 of each of the respective number of hollow fluid conduits 102. Each of the hollow fluid conduits 102 is fluidly coupled to the interior space 106 within the vessel 108, thereby permitting a free flow of the multi-phase mixture from the downward flow path 114 to the upward flow path 118.

In at least some instances, the aggregate transverse cross-sectional area of the number of hollow fluid conduits 102 is about 90% or less of the transverse cross-sectional area of the vessel 108; about 75% or less of the transverse cross-sectional area of the vessel 108; about 50% or less of the transverse cross-sectional area of the vessel 108; about 25% or less of the transverse cross-sectional area of the vessel 108; about 15% or less of the transverse cross-sectional area of the vessel 108; or about 10% or less of the transverse cross-sectional area of the vessel 108.

One or more liquids may be introduced to the downward flow path 114 using the one or more liquid distributors 130 that are positioned in or fluidly coupled to the downward flow path 114. Such liquids can include any liquid media capable of supporting or transporting dissolved or suspended sustenance or nutrients to the microbiological organisms forming the biomass within the fermentor 100. One or more gases, substrate gases, or combinations thereof may be introduced to the downward flow path 114 via the one or more gas distributors 132 that are positioned in or fluidly coupled to the downward flow path 114. Such gases can include a single gas or a combination of gases capable of supporting or providing sustenance or nutrients to the biological organisms within the fermentor 100. In at least some instances, such gases may include one or more inert gases, for example nitrogen. In at least some instances, a plurality of gases, a plurality of substrate gases, or some combination thereof may be introduced separately to the downward flow path 114 to advantageously reduce or even preclude the formation of explosive gas mixtures outside of the fermentor 100. For example, where an inflammable $C_1$ compound (e.g., methane) is used to provide at least a portion of a gaseous substrate for the biological organisms within the fermentor 100 and where air is used to provide oxygen to the biological organisms within the fermentor 100, the gas containing the inflammable $C_1$ compound may be introduced using a first gas distributor 132a and the air introduced using a second, physically distinct or separate, gas distributor 132b to avoid mixing of the $C_1$ compound and the air outside of the fermentor 100. The introduction of one or more liquids and one or more gases to the downward flow path 114 creates a downward flow 116 of a multi-phase fluid within the downward flow path 114. Biological growth occurring within the downward flow path 114 can absorb oxygen, nutrients and $C_1$ compounds from the downward flow 116 of multi-phase fluid in the downward flow path 114.

The contemporaneous introduction of one or more inflammable $C_1$ compounds and an oxygen containing gas into the fermentor 100 may result in the formation of flammable or explosive gas mixtures within the fermentor 100. To reduce the possibility of such an occurrence, the downward flow path 114 and the upward flow path 118 may be of a physical shape or configuration such that both remain "fluid full" when liquid is introduced to the fermentor 100 via the one or more liquid distributors 130 (i.e., gas accumulation points within the downward flow path 114 and the upward flow path 118 are minimized, or more preferably, eliminated). In at least some instances, one or more gas relief devices or liquid/gas separation devices (not shown in FIG. 1) may be fluidly coupled to the downward flow path 114, the upward flow path 118 or both to remove accumulated gases from the fermentor 100. Such removed gases may be partially or completely recovered and partially or completely recycled to the fermentor 100 or may be flared or otherwise safely disposed of.

Each of the number of hollow fluid conduits 102 can have the same or different transverse cross-sectional profile. Example hollow fluid conduit 102 transverse cross-sectional profiles include, but are not limited to, a circular transverse cross-sectional profile, a rectangular or square transverse cross-sectional profile, or a triangular transverse cross-sectional profile (i.e., a profile taken transverse to the longitudinal axis of the hollow fluid conduit 102). In some instances, more than one type of hollow fluid conduit 102 may be used within a single fermentor 100. For example, a portion of the number of hollow fluid conduits 102 in the fermentor 100 may have a circular transverse cross-sectional profile, while the remaining portion of the hollow fluid conduits 102 have a square transverse cross-sectional profile.

All or a portion of the hollow fluid conduits 102 can include one or more embossed or debossed surface features useful in supporting, promoting, or otherwise fostering the growth of biological organisms. All or a portion of the hollow fluid conduits 102 can include one or more embossed or debossed surface features useful in promoting or otherwise enhancing turbulence or heat transfer to the respective thermal transfer surface(s) 128, 140 in the downward flow path 114, the upward flow path 120, or both. All or a portion of the hollow fluid conduits 102 can include one or more baffles to increase turbulence within the upward flow path 118, such increases in turbulence can advantageously improve mass transfer within the upward flow path 118 as well as increase the residence time of gas substrate bubbles present in the upward flow path 118.

In some instances, the longitudinal axis of each of the number of hollow fluid conduits 102 is aligned parallel to the longitudinal axis of every other hollow fluid conduit 102 disposed in the vessel 108. In some instances, the longitudinal axis of each of the number of hollow fluid conduits 102 is parallel to the longitudinal axis of the vessel 108. In some instances, the longitudinal axis of each of all or a portion of the number of hollow fluid conduits 102 is parallel to and coaxially aligned with the longitudinal axis of the vessel 108.

Each of the hollow fluid conduits 102 can have the same or a different length. In some instances, at least a portion of the number of hollow fluid conduits 102 may extend to or even beyond the bottom 124 of the vessel 108. In such instances, the downward flow path 114 may be fluidly coupled to the upward flow path 118 via one or more external fluid conduits, for example via one or more piping networks positioned external to the vessel 108. Each of the hollow fluid conduits 102 can have a length of from about 6 inches to about 240 inches; from about 12 inches to about 192 inches; or from about 24 inches to about 144 inches.

Each of the number of hollow fluid conduits 102 may be a metallic, non-metallic, or composite structure. For example, each of the hollow fluid conduits 102 may include one or more metallic materials such as 304, 304L, 316, or 316L stainless steels. In some instances, one or more coatings, layers, overlays, inserts, or other materials may be deposited on, applied to, joined with, or formed integral to all or a portion of each of the number of hollow fluid conduits 120 to beneficially or detrimentally affect the ability for microbiological organisms to attach thereto or to grow thereupon. For example, a coating inhibiting the growth or attachment of microbiological organisms may be deposited on or formed integral with the portion of the hollow fluid conduits 102 that are thermally conductively coupled to the thermal transfer surfaces 128. In another example, a coating that promotes the growth or attachment of biological organisms may be deposited on or formed integral with the hollow fluid conduits 102 in areas where removal of accumulated biomass is more easily accomplished.

In at least some instances, each of the hollow fluid conduits 102 includes a substantially rectangular or square hollow member having an aperture extending along the longitudinal axis of the conduit. In other instances, each of the hollow fluid conduits 102 includes a substantially cylindrical hollow member having an aperture extending along the longitudinal axis of the conduit. The inside and outside diameters of such square or cylindrical hollow fluid conduits 102 may be continuous or constant along the axial length of the conduit or may vary along the axial length of the conduit. For example, the inside and outside diameters of a cylindrical hollow fluid conduit 102 may increase co-currently along the upward flow path 118 such that the fluid velocity along the upward flow path decreases from the inlet to the outlet of the hollow fluid conduit 102. Cylindrical hollow fluid conduits 102 can have an inside diameter of from about 2 inches to about 240 inches; from about 4 includes to about 192 inches; from about 6 inches to about 144 inches; from about 8 inches to about 120 inches; or from about 12 inches to about 96 inches. Rectangular or square hollow fluid conduits 102 can have a diagonal of from about 2 inches to about 240 inches; from about 4 includes to about 192 inches; from about 6 inches to about 144 inches; from about 8 inches to about 120 inches; or from about 12 inches to about 96 inches.

In at least some instances, the construction of the hollow fluid conduits 102, vessel 108, or both, may include features that facilitate sterilization of all or a portion of the process contact surfaces. Such sterilization can be accomplished for example using steam sterilization, ultraviolet sterilization, chemical sterilization, or combinations thereof. In at least some instances, one or more non-metallic materials or one or more non-metallic coatings may be used within all or a portion of the interior or exterior of some or all of the number of hollow fluid conduits 102. The use of such non-metallic materials may advantageously provide, for example, sterilizable surfaces that are capable of supporting or promoting biological growth.

All or a portion of the number of hollow fluid conduits 102 may optionally include one or more thermal energy transfer surfaces 128 useful in limiting heat buildup within either or both the downward flow path 114 or the upward flow path 120. The thermal energy transfer surfaces 128 can include one or more conduits or reservoirs disposed along the interior perimeter 152, the exterior perimeter 154, or both the interior and exterior perimeter of the hollow fluid conduit 102. The one or more conduits or reservoirs can include any device or system through which one or more thermal transfer media can flow. In at least some instances, the one or more thermal energy transfer surfaces 128 can be formed integrally with the hollow fluid conduit 102, forming at least a portion of the conduit. In one example, the thermal energy transfer surface 128 can include one or more reservoirs through which a thermal transfer fluid can flow or circulate, and which is thermally conductively coupled to at least a portion of the hollow fluid conduit 102. In another example, the thermal energy transfer surface 128 can include one or more pipe or tubing coils or similar structures through which a thermal transfer fluid can flow or circulate, and which is thermally conductively coupled to at least a portion of the hollow fluid conduit 102. The thermal transfer media can include any material, including gases or liquids, that are capable of either providing thermal energy to or removing thermal energy from either or both the downward flow path 114 or the upward flow path 118. Example thermal transfer media include, but are not limited to, cooling water, chilled water, and steam.

Each of the hollow fluid conduits 102 can be permanently or detachably attached to the vessel 108. In at least some instances, the hollow fluid conduit multi-phase mixture discharge fluid connections 138 may be attached or otherwise affixed to the top 126 of the vessel 108 to allow the multi-phase mixture 136 flowing through the upward flow path 118 to exit each of the number of hollow fluid conduits 102.

The height of the vessel 108 can be the same as or different from the length of all or a portion of the number of hollow fluid conduits 102. Where the height of the vessel 108 is less than the length of all or a portion of the number of hollow fluid conduits 102, all or a portion of the hollow fluid conduits 102 may project from the bottom 124 of the vessel 108, top 126 of the vessel 108, or both the top and the bottom of the vessel 108. The vessel 108 can have a height of from about 6 inches to about 240 inches; from about 12 inches to about 192 inches; or from about 24 inches to about 144 inches.

The vessel 108 can have a regular or an irregular transverse cross-sectional profile (i.e., a profile taken transverse to the longitudinal axis of the vessel 108). Example vessel 108 transverse cross-sectional profiles include, but are not limited to, a circular transverse cross-sectional profile, a square transverse cross-sectional profile, or a triangular transverse cross-sectional profile. For example the transverse cross sectional profile of the vessel 108 may decrease co-current with the downward flow path 114 such that the fluid velocity and pressure of the multi-phase mixture increases along the downward flow path 114.

All or a portion of the wall(s) 110, bottom 124, or top 126 of the vessel 108 may optionally include one or more thermal energy transfer surfaces 140 useful in limiting heat buildup within the downward flow path 114. The thermal energy transfer surfaces 140 can include one or more conduits or reservoirs thermally conductively coupled to at least a portion of the downward flow paths 114 within vessel 108 and through which one or more thermal transfer media can flow. For example, the thermal energy transfer surfaces 140 can include one or more reservoirs through which a thermal transfer fluid can flow or circulate. In another example, the thermal energy transfer surfaces 140 can include one or more pipe or tubing coils or similar structures through which a thermal transfer fluid can flow or circulate. The thermal transfer media can include any material, including gases or liquids, capable of either providing thermal energy to or removing thermal energy from the downward flow path 114. Example thermal transfer media include, but are not limited to, cooling water, chilled water, and steam.

In at least some instances, the vessel 106 may be a metallic, non-metallic, or composite structures. Example metallic structures include vessel walls, top and bottom surfaces fabricated from materials such as 304, 304L, 316, or 316L stainless steels. Example non-metallic structures include, but are not limited to, fiberglass, fiberglass reinforced plastic (FRP), polyethylene, and the like. Example composite structures include, but are not limited to, metal reinforced FRP and the like. In some instances, one or more coatings or other materials may be formed integral with or applied to the vessel 108 to variously affect the ability for microbiological organisms to attach thereto. For example, a coating inhibiting the growth or attachment of microbiological organisms may be deposited on or formed integral with the vessel 108 in areas occupied by thermal transfer surfaces 140. In another example, a coating that promotes the growth or attachment of microbiological organisms may be deposited on or formed integral with the vessel 108 in areas where removal of accumulated biomass is more easily accomplished.

One or more liquid distributors 130 are disposed either within the downward flow path 114, within the upward flow path 118, fluidly coupled to the downward flow path 114, fluidly coupled to the upward flow path 120, or combinations thereof. The one or more liquid distributors 130 can include any device, structure or system capable of distributing fluid in any desired pattern within the selected flow path. In some instances, all or a portion of the one or more liquid distributors 130 can include a pipe or distribution plate containing a number of orifices or apertures through which fluid enters the respective flow path. In some instances, all or a portion of the one or more liquid distributors 130 can include a fluid connection such as a nozzle or coupling disposed at an appropriate location on the vessel 108. In at least some instances, liquid distributors 130 may be positioned at multiple locations within either or both the downward flow path 114, the upward flow path 120, or both. The use of liquid distributors 130 positioned at multiple locations within the downward flow path 114 and/or the upward flow path 120 advantageously permits the introduction of liquids containing one or more components useful in promoting one or more desirable qualities in the accumulated biomass. For example, a liquid containing one or more growth promoting components may be introduced using a first liquid distributor 130*a* positioned in the downward flow path 114 and a liquid containing one or more components that increase the production of one or more desired compounds may be introduced using a second liquid distributor 130*b* positioned at a later point in the downward flow path 114 or in the upward flow path 120.

The one or more liquid distributors 130 are sized or selected based upon expected flow, operating temperature, operating pressure, and allowable pressure drop. The liquid distributors 130 may include a number of orifices through which liquid in the distributor exits, such orifices can be sized and positioned based upon a defined flow range and an allowable pressure drop range. In some instances, liquid exiting the one or more liquid distributors 130 may flow through one or more dispersion or mixing devices that promote dispersion of or mixing between the liquid exiting the distributor 130 and the multi-phase mixture flowing through the respective flow path.

One or more gas distributors 132 are disposed either within or in fluid contact with the downward flow path 114, the upward flow path 120, or both. The one or more gas distributors 132 can include any device, structure or system capable of distributing in any defined pattern one or more gases having a defined physical gas bubble size or shape within the selected flow path. In some instances, all or a portion of the one or more gas distributors 132 can include a pipe or distribution plate containing a number of orifices or apertures through which a gas, a gas substrate, or combinations thereof are introduced to the flow path. In some instances, all or a portion of the one or more gas distributors 132 can include a sintered metal or porous ceramic distribution plate capable of producing a multitude of fine gas bubbles within the selected flow path. In at least some instances, gas distributors 132 may be positioned at multiple locations within either or both the downward flow path 114, the upward flow path 118, or both.

Gas substrate bubbles may be introduced at a location near the liquid distributor 130 (i.e., at the start of the downward flow path 114). The introduction of gas substrate bubbles at a location near the liquid distributor 130 advantageously permits pushing of the gas substrate bubbles along the downward flow path 114 by the flow of the multi-phase mixture through the downward flow path 114. Passing the gas substrate bubbles downward along the downward flow path 114 may advantageously improve mass transfer, as the gas substrate bubble size will tend to decrease with the increase in pressure along the downward flow path 114 attributable to the increasing hydrostatic head. The gas substrate bubbles present in the downward flow 116 of the multi-phase mixture will tend to get smaller as they travel along the downward flow path 114 and through the fermentor 100. Advantageously, shear forces and heat generation within the fermentor 100 are reduced since a conventional agitator is not needed to disperse the gas substrate bubbles or to maintain the dispersion of the gas substrate bubbles present in the multi-phase mixture within the fermentor 100.

The use of gas distributors 132 positioned at multiple locations within the downward flow path 114 and/or the upward flow path 120 advantageously permits the introduction of gaseous substrates containing one or more components useful in promoting one or more desirable qualities in the accumulated biomass. For example, a gas substrate containing one or more growth promoting components may be introduced using a first gas distributor 132a positioned in the downward flow path 114 and a gas substrate containing one or more components that increase the production of one or more desired compounds may be introduced using a second gas distributor 132b positioned at a later point in the downward flow path 114 or in the upward flow path 120. In at least some instances, the gas distributor 132 can provide gas substrate bubbles having a diameter of from about 0.01 inches to about 1 inch; from about 0.05 inches to about 0.75 inches; from about 0.075 inches to about 0.75 inches; or from about 0.1 inches to about 0.5 inches.

Figure 2:
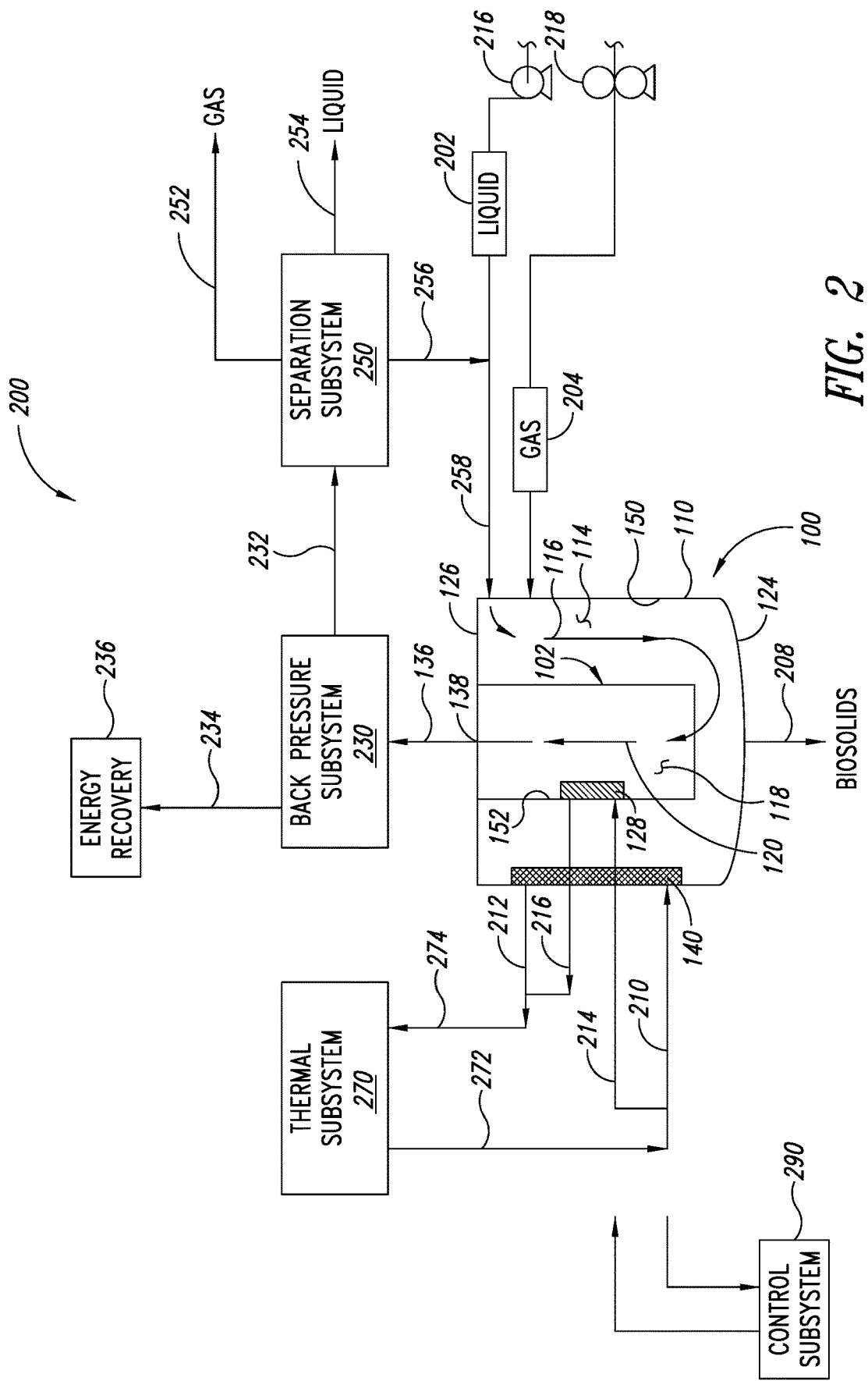
FIG. 2 shows a block flow diagram of an example fermentation system including optional cooling subsystem, backpressure subsystem, and separation subsystem that alone or in combination are useful in fermenting a gaseous substrate to provide one or more gaseous or liquid $C_2$ or higher hydrocarbons, according to one or more illustrated embodiments.

FIG. 2 shows an example fermentation system 200 that includes a fermentor 100 along with an optional backpressure subsystem 230, a separation subsystem 250, and an optional thermal subsystem 270. Although shown as an integrated system 200, the optional subsystems may be installed or otherwise combined with the fermentor 100 either individually or in any combination. One or more liquids 202 and one or more gas substrates 204 are introduced to the fermentor 100 to form a multi-phase mixture therein that travels through the fermentor 100 via the downward flow path(s) 114 and the upward flow path(s) 118. After passage through the fermentor 100, the multi-phase fluid may contain one or more compounds produced by the biological organisms within the fermentor 100, unconsumed nutrients and other compounds in the liquid within the multi-phase mixture, unconsumed gases in the gas bubbles within the multi-phase mixture, and microbiological organisms in the form of biosolids. Excess microbiological organisms may be removed from the fermentor 100 as biomass either intermittently or continuously via at least one biomass removal fluid connection 208. Biomass accumulations within the fermentor 100 may be removed to maintain the overall biomass within the fermentor 100 within a defined range or above or below a defined threshold. In at least some instances, biomass removed from the fermentor 100 via the at least one biomass removal fluid connection 208 may include one or more useful compounds. For example, the biological organisms within the excess biomass may contain an amount of one or more intracellular lipids or similar compounds useful in the production of a biofuel such as biodiesel.

The one or more liquids 202 may include any liquid suitable for sustaining or delivering one or more nutrients to the microbiological organisms within the fermentor 100. Such liquids 202 may include, but are not limited to, solutions containing water, one or more alcohols, minerals, one or more nitrogen containing compounds, one or more phosphorus containing compounds, and the like. In at least some instances, one or more fluid movers 216 are used to deliver the one or more liquids 202 to the one or more liquid distributors 130 either in or fluidly coupled to the fermentor 100 in a controlled manner and at a pressure that is greater than atmospheric pressure. The one or more fluid movers 216 can include any type of pump or similar device capable of transferring a liquid between two points. Example fluid movers 216 include, but are not limited to, centrifugal pumps, positive displacement pumps, progressing cavity pumps, double diaphragm pumps, and the like. Other illustrative fluid movers 216 include, but are not limited to, eductors, ejectors, and similar devices. The transfer of liquid 202 to the fermentor 100 can be flow controlled, pressure controlled, or controlled using combinations of pressure, temperature, flow, level, flowrate, superficial velocity, or compositional analysis process variable data gathered from one or more points within the fermentor 100 or from one or more points within the fermentation system 200. In at least some instances, the transfer of liquid 202 by the fluid mover 216 can be controlled based on the measured concentration of one or more components or compounds (e.g., one or more nitrogen containing nutrients) within the fermentor 100, for example, the flow of liquid 206 transferred by the fluid mover 216 may be increased in response to a measured decrease in nutrient concentration within the fermentor 100.

In at least some instances, the flowrate of the liquid transferred by the fluid mover 216 can be based in whole or in part on maintaining the velocity of the downward fluid flow 116 in the downward flow path 114 within a defined range that is able to transport the gas bubbles present in the multi-phase mixture downwardly along the downward flow path 114. The velocity of the downward flow 116 in the downward flow path 114 can be measured using one or more contact or non-contact flow sensors. Example flow sensors can include, but are not limited to, magnetic flowmeters, Doppler flowmeters, mass flowmeters, and the like. In such instances, the downward flow 116 in the downward flow path 114 can have a velocity of from about 0.1 feet/second (f/s) to about 15 f/s; from about 0.2 feet/second (f/s) to about 10 f/s; or from about 0.5 feet/second (f/s) to about 5 f/s.

Although depicted on the inlet side of the fermentor 100, the fluid mover 216 may be disposed at any location where providing a downward flow 116 in the downward flow path 114 and an upward flow 120 in the upward flow path 118 is possible. For example, as shown in FIG. 2, the fluid movers 216 may be fluidly coupled to the inlet of the fermentor 100 to provide a forced downward flow 116 through the downward flow path 114 and a forced upward flow 120 through the upward flow path 118. In another example, all or a portion of the fluid movers 216 may be fluidly coupled between the downward flow path 114 and the upward flow path 118 to provide an induced downward flow 116 along the downward flow path 114 and a forced upward flow 120 along the upward flow path 118. In yet another example, all or a portion of the fluid movers 216 may be fluidly coupled to the multi-phase mixture discharge fluid connection 138 to induce a downward flow 116 through the downward flow path 114 and to induce an upward flow 120 through the upward flow path 118.

The one or more gas substrates 204 can include any gas, gases, or combination of gases suitable for sustaining or delivering one or more nutrients to the biological organisms within the fermentor 100. Such gases can include, but are not limited to, one or more gases containing carbon compounds. Such gases can include, but are not limited to, one or more gases containing $C_1$ carbon compounds such as methane or carbon monoxide. The one or more gas substrates 204 may also include one or more gases used in the metabolic processes of the biological organisms within the fermentor 100. Such gases can include, but are not limited to, oxygen, oxygen containing compounds and hydrogen. The one or more gas substrates 204 may be transferred to the fermentor 100 as a pure gas or as a gas mixture (e.g., syngas—a mixture of carbon monoxide and hydrogen). The one or more gas substrates 204 may be transferred to the fermentor 100 individually (e.g., methane and an oxygen containing gas such as air may be transferred individually to minimize the likelihood of formation of an explosive gas mixture external to the fermentor 100).

The one or more gas substrates 204 may optionally be transferred to the fermentor 100 using a gas mover 218. Example gas movers 218 include, but are not limited to, rotary lobe compressors, centrifugal compressors, screw compressors, and the like. The delivery pressure of the one or more gas substrates 204 depends upon a variety of factors including the operating pressure of the fermentor 100 and the pressure drop associated with the gas distributor 132 used to distribute the one or more gas substrates 204 within the downward flow path 114. Similarly, the delivery flowrate of the one or more gas substrates may be manually or automatically controlled to maintain the concentration or level of dissolved gas within the fermentor 100 within a defined range (e.g., dissolved oxygen above at least 4 ppm) based at least in part on the needs of the biological organisms present in the fermentor 100. In at least some instances, the one or more gas substrates 204 can be delivered to the fermentor 100 at a pressure of from about 5 psig to about 600 psig; from about 5 psig to about 600 psig; from about 25 psig to about 400 psig; or from about 50 psig to about 300 psig.

Any number of gases may be introduced through a common gas distribution header 132 or any number of individual gas distribution headers 132. Such gas distribution headers may introduce all of the gas substrate 204 at a single point within the fermentor 100 or may introduce portions of the gas substrate 204 at various locations throughout the fermentor 100. In at least some instances, the gas substrate 204 can include, but is not limited to, methane, carbon monoxide, hydrogen, or oxygen. In at least some instances, the feed rate of the gas substrate 204 can be referenced to the feed rate of the liquid media 202. For example, methane may be introduced as a gas substrate 204 at a rate of from about 0.1 grams of methane/liter of liquid media (g/l) to about 100 g/l; from about 0.5 g/l to about 50 g/l; or from about 1 g/l to about 25 g/l. Carbon monoxide ("CO") may be introduced as a gas substrate 204 at a rate of from about 0.1 grams of CO/liter of liquid media (g/l) to about 100 g/l; from about 0.5 g/l to about 50 g/l; or from about 1 g/l to about 25 g/l. Oxygen may be introduced as a gas substrate 204 at a rate of from about 1 grams of oxygen/liter of liquid media (g/l) to about 100 g/l; from about 2 g/l to about 50 g/l; or from about 5 g/l to about 25 g/l. Hydrogen may be introduced as a gas substrate 204 at a rate of from about 0.01 grams of hydrogen/liter of liquid media (g/l) to about 50 g/l; from about 0.1 g/l to about 25 g/l; or from about 1 g/l to about 10 g/l.

Within the fermentor 100 the microbiological organisms will metabolize at least a portion of the carbon containing compounds present in the multi-phase mixture. At least a portion of this process may include the production of additional microbiological organisms that increase the overall quantity of biomass present in the fermentor 100. Left uncontrolled, the biomass within the fermentor 100 can accumulate to a point such that one or more operational aspects of the fermentor 100 (e.g., flowrate, pressure drop, production of desired products, etc) is compromised or adversely affected by the presence of the excess biomass. In such instances, the ability to remove at least a portion of the biomass present in the fermentor 100 is desirable. In at least some instances, at least a portion of the floor 124 of the fermentor 100 may be sloped (e.g., a cone bottom) or shaped (e.g., an ASME dished head) such that biomass preferentially accumulates at a location within the fermentor 100 facilitating biosolids removal from the fermentor 100 via the at least one biomass removal fluid connection 208. For example, an ASME dished head may facilitate the accumulation of biosolids at a central location of the head proximate a fluid connection or similar device that permits the removal of the biosolids 208 from the fermentor 100 via the at least one biomass removal fluid connection 208.

The backpressure subsystem 230 can include any number of devices, systems, or combinations thereof to maintain the pressure within the fermentor 100 within a defined range. For example, the backpressure subsystem 230 may maintain the pressure in the fermentor 100 in a range that is at or above atmospheric pressure. In at least some instances, the backpressure subsystem 230 can maintain an upstream pressure (i.e., pressure in the fermentor 100) of from about 1 psig to about 150 psig; about 1 psig to about 100 psig; about 1 psig to about 75 psig; about 1 psig to about 50 psig; or about 1 psig to about 25 psig. Maintaining the fermentor 100 at a pressure greater than atmospheric pressure may advantageously improve the rate of mass transfer between the gas substrate bubbles, the liquid media, and consequently the microbiological organisms within the fermentor 100 by maintaining the partial pressure of gases used in the metabolic processes of the microbiological organisms at an elevated level in the fermentor 100 (i.e., gas substrate partial pressures greater than those achievable at atmospheric pressure).

At least a portion of the multi-phase mixture 136 that exits the fermentor 100 is received by the backpressure subsystem 230. The flowrate of the multi-phase mixture 136 exiting the fermentor 100 may be manually or automatically controlled. For example, the flowrate of the multi-phase mixture 136 exiting the fermentor 100 may be measured using a process element (not shown in FIG. 2) such as a mass flowmeter, a magnetic flowmeter, an ultrasonic flowmeter, or similar. Such flow measurement can provide one or more signals containing data representative of the multi-phase mixture discharge 136 flow, velocity, pressure, composition, or combinations thereof to a control subsystem 290. The control subsystem 290 can include a local controller, a central control system, or distributed control system capable of providing a control output to a final control element such as a control valve (not shown in FIG. 2). The multi-phase mixture discharge 136 passes through the backpressure subsystem 230 and exits as a low pressure multi-phase mixture 232. In at least some instances, the backpressure subsystem 230 can maintain an downstream pressure (i.e., pressure to the separation subsystem 250) and the low pressure multi-phase mixture 232 can have a pressure of from about 1 psig to about 150 psig; about 1 psig to about 100 psig; about 1 psig to about 75 psig; about 1 psig to about 50 psig; or about 1 psig to about 25 psig.

The backpressure subsystem 230 can include any number of pressure reducing devices including, but not limited to, orifices, pressure reducing valves, turbines, or any other device or system capable of providing a known, controllable, pressure drop. In some instances, the pressure within the fermentor 100 may be manually or automatically varied, controlled, or adjusted based upon one or more control inputs provided to the backpressure subsystem 230. In at least some instances, the backpressure subsystem 230 can include one or more turbines or similar devices that are capable of providing a shaft output 234. Such a shaft output 234 may be used as an input to an energy recovery device 236, for example a generator capable of providing electrical power for local consumption or provision to a local commercial, industrial, or residential electric distribution network.

The separation subsystem 250 can include any number of devices, systems, or combinations thereof to separate the low pressure multi-phase mixture 232 into at least a gas effluent 252 and a liquid effluent 254. In at least some instances, biosolids present in the low pressure multi-phase mixture 232 may be separated into a solids-containing effluent 256. In at least some instances, at least a portion of the solids-containing effluent 256 from the separation subsystem 250 can be combined with the one or more liquids 202 to provide a mixture 258 for return to the fermentor 100. In at least some instances, the separation subsystem 250 can include one or more separators having an aggregate volume of at least about 10% of the volume of the vessel 108; at least about 20% of the volume of the vessel 108; at least about 20% of the volume of the vessel 108; or at least about 40% of the volume of the vessel 108.

The separation subsystem 250 can include one or more passive separators (e.g., one or more wet cyclones or the like) capable of separating the gas effluent 252 and the liquid effluent 254 from the low pressure multi-phase mixture 232. In at least some instances, the passive separator may also include a solids separation section to separate at least a portion of the biosolids present in the low pressure multi-phase mixture 232. In other instances, the separation subsystem 230 may include one or more active separation devices (e.g., a three phase rotary separator) capable of separating the gas effluent 252, the liquid effluent 254, and the solids-containing effluent from the low pressure multi-phase mixture 232.

In at least some instances, the gas effluent 252 may include a mixture of one or more gas substrates (e.g., methane or carbon monoxide) and one or more gaseous byproducts (e.g., carbon dioxide) generated as a byproduct by the biological organisms in the fermentor 100. In at least some instances, the gas effluent 252 may be separated (not shown in FIG. 2) and at least a portion of the one or more gas substrates recycled to the fermentor 100 for example as a gas substrate 204. In at least some instances, the gas effluent 252 may include one or more useful compounds. For example, the gas effluent 252 may contain an amount of one or more gaseous $C_{2+}$ hydrocarbon compounds including, but not, limited to ethane, ethylene, propane, butane, and compounds based thereupon having value as either a finished product or as a raw material in a subsequent process. Such useful compounds may be separated from the gas effluent 252 prior to recycling at least a portion of the gas effluent 252 to the fermentor 100.

In at least some instances, the liquid effluent 254 may include a mixture containing one or more liquids, nutrients, and the like introduced to the fermentor with the liquid 202. In such instances, at least a portion of the liquid effluent 254 can be separated (not shown in FIG. 2) and recycled to the fermentor 100 for example as a liquid media 202. In at least some instances, the liquid effluent 254 may include one or more useful compounds. For example, the liquid effluent 254 may contain an amount of one or more liquid $C_{2+}$ hydrocarbon compounds including, but not, limited to alcohols, ketones, glycols, and other compounds based thereupon having value as either a finished product or as a raw material in a subsequent process. Such useful hydrocarbon compounds may be separated from the liquid effluent 254 prior to disposing of the liquid effluent 254 or recycling at least a portion of the liquid effluent 254 back to the fermentor 100.

In at least some instances, the solids-containing effluent 256 may include a slurry or mixture containing one or more liquids and biomass removed from the fermentor 100. In such instances, it may be desirable to recycle at least a portion of the solids-containing effluent 256 back to the fermentor 100. The recycle of biomass to the fermentor 100 may advantageously serve to reseed the microbiological colony within the fermentor 100. Although not shown in FIG. 2, at least a portion of the solids-containing effluent 256 can be recycled directly to the downward flow path 114 in the fermentor 100. At least a portion of the solids-containing effluent 256 can be mixed with the one or more liquids 202 and recycled to the fermentor 100. In at least some instances, the solids-containing effluent 256 may include one or more useful compounds. For example, the biological organisms within the solids-containing effluent 256 may contain an amount of one or more intracellular lipids or similar compounds useful in the production of a biofuel such as biodiesel. Although not shown in FIG. 2, in such instances, at least a portion of the solids-containing effluent 256 may be removed from the separation subsystem 230 for subsequent processing into one or more desired products.

The thermal subsystem 270 can include any number of devices, systems, or combinations thereof to add thermal energy to or to remove thermal energy from the multiphase fluid in the fermentor 100. In at least some instances, the fermentation that occurs within the fermentor 100 generates heat as a byproduct. Left uncontrolled, such heat can adversely affect the metabolism or health of the microbiological organisms within the fermentor 100. Alternatively, microbiological organisms may also have a temperature below which the metabolism or health of the organism is adversely affected. As such, the biological organisms within the fermentor 100 have a defined temperature range providing optimal growth and metabolic conditions. In at least some instances, the multi-phase mixture within the fermentor 100 can be maintained at a temperature of about 130° F. or less; about 120° F. or less; about 110° F. or less; about 100° F. or less; about 95° F. or less; about 90° F. or less; about 85° F. or less; or about 80° F. or less using the thermal subsystem 270. In at least some instances, the multi-phase mixture within the fermentor 100 can be maintained at a temperature of from about 55° F. to about 120° F.; about 60° F. to about 110° F.; about 110° F. to about 120° F.; about 100° F. to about 120° F.; about 65° F. to about 100° F.; about 65° F. to about 95° F.; or about 70° F. to about 90° F. using the thermal subsystem 270.

In at least some instances, one or more thermal transfer surfaces 128 may be disposed at least partially within the downward flow path 114 to alter, adjust, or control the temperature of the downward flow 116 of the multi-phase mixture therein. Similarly, one or more thermal transfer surfaces 140 may be disposed at least partially within the upward flow path 118 to alter, adjust, or control the temperature of the upward flow 120 of multi-phase mixture therein.

In at least some instances, such thermal transfer surfaces 128, 140 may include one or more piezoelectric surfaces which provide cooling upon passage of an electric current therethrough. Such thermal transfer surfaces 128, 140 may include one or more resistive surfaces (e.g., Calrod heaters) which provide heating to increase the temperature of the multi-phase mixture upon passage of an electric current therethrough. In such instances, the thermal subsystem 270 can include one or more systems to control the flow of electrical power to the thermal transfer surfaces 128, 140 based at least in part on the measured temperature of the multi-phase mixture in the fermentor 100.

In other instances, such thermal transfer surfaces 128, 140 can include a number of reservoirs or conduits positioned within the downward flow path 114, the upward flow path 120 or both, and through which thermal transfer media at either a reduced temperature or an elevated temperature is circulated to variously cool or heat the multi-phase mixture in the fermentor 100. The thermal transfer media can include any fluid, liquid, or gas capable of transporting or otherwise conveying thermal energy to or thermal energy from the multi-phase mixture in the fermentor 100. In such instances, the thermal subsystem 270 can include one or more systems or devices to remove thermal energy from the thermal transfer media (e.g., for cooling the multi-phase mixture in the fermentor 100) or impart thermal energy to the thermal transfer media (e.g., for warming the multi-phase mixture in the fermentor 100).

In at least one instances, the thermal transfer media can include water or an aqueous solution of water and one or more corrosion, scale, and microbiological inhibitors. In such instances, the thermal subsystem 270 can include one or more systems for removing thermal energy from the thermal transfer media to cool the multi-phase mixture. For example, an open-loop evaporative cooling tower or a closed loop air cooler may be used to cool the thermal transfer media. In such instances, the thermal subsystem 270 may optionally include one or more systems for imparting thermal energy to the thermal transfer media to warm the multi-phase mixture. For example, a natural gas or electric water heater or furnace may be used to warm the thermal transfer media.

The thermal transfer media can be provided by the thermal subsystem 270 via one or more thermal media distribution networks 272. The one or more thermal media distribution networks 272 can include an electrical distribution network where electric heating and cooling thermal transfer surfaces 128, 140 are provided. The one or more thermal media distribution networks 272 can include a network of fluid conduits where a liquid thermal transfer media (e.g., water) is provided to the thermal transfer surfaces 128, 140. Branches 210, 214 from the thermal media distribution network 272 can be used to supply thermal transfer media to the thermal transfer surfaces 128, 140. For example, a branch 210 can be used to supply thermal transfer media from the thermal media distribution network 272 to the thermal transfer surface 128 disposed in the downward flow path 114, and a branch 214 can be used to supply thermal transfer media from the thermal media distribution network 272 to the thermal transfer surface 140 disposed in the upward flow path 120.

The thermal transfer media can be collected and at least partially returned to the thermal subsystem 270 via one or more thermal media collection networks 274. The one or more thermal media collection networks 274 can include a collection of networked fluid conduits 212, 216 where a liquid thermal transfer media (e.g., water) is removed from the thermal transfer surfaces 128, 140. Branches from the thermal media collection network 274 can be used to collect thermal transfer media from the thermal transfer surfaces 128, 140. For example, a branch 212 can be used to return thermal transfer media from the thermal transfer surface 128 disposed in the downward flow path 114 to the thermal media collection network 274, and a branch 216 can be used to return thermal transfer media from the thermal transfer surface 140 disposed in the upward flow path 120 to the thermal media collection network 274.

In at least some instances, all or a portion of the fermentation process may be at least partially automatically controlled using a control subsystem 290. The control subsystem 290 may collect process related information provided by one or more process elements in the form of signals containing analog or digital data representing one or more process variables. For instance, the control subsystem can collect process related signals using one or more process elements including, but not limited to, mass flow sensors, volumetric flow sensors, temperature sensors, pressure sensors, level sensors, analytical sensors (e.g., dissolved oxygen sensors, biological oxygen demand or "BOD" sensors, pH sensors, conductivity sensors, and the like) or any other device capable of providing a signal containing data representative of one or more process related condition within the fermentor 100.

The control subsystem 290 may execute one or more sets of instructions controlling, altering, or adjusting one or more aspects of the fermentation process based at least in part on the process variable signals received from the process elements. Such instructions may result in the generation of one or more control output signals by the control subsystem 290. The control output signals can be transmitted from the control subsystem 290 to one or more final control elements such as block valves, control valves, motors, variable speed drives, etc. The interaction between the final control elements and the fermentation process can, in turn, provide the control subsystem 290 with a high degree of relatively accurate control of the fermentation process.

For example, responsive to the receipt of one or more signals containing data indicative of the temperature of the multi-phase mixture in the fermentor 100, the control subsystem 290 may initiate, alter, or cease the flow of thermal transfer media to one or more thermal transfer surfaces 128, 140. Similarly, responsive to the receipt of one or more signals containing data indicative of the dissolved oxygen level of the multi-phase mixture in the fermentor 100, the control subsystem 290 may increase, decrease, or maintain the flow of the oxygen containing gas substrate 204 to the fermentor 100. Although only two illustrative examples are provided herein, any flow, level, pressure, analytical value, or the like that is appropriate to the fermentation process may be similarly controlled by the control subsystem 290 using one or more appropriate process sensors and one or more appropriate final control elements.

Figure 3:
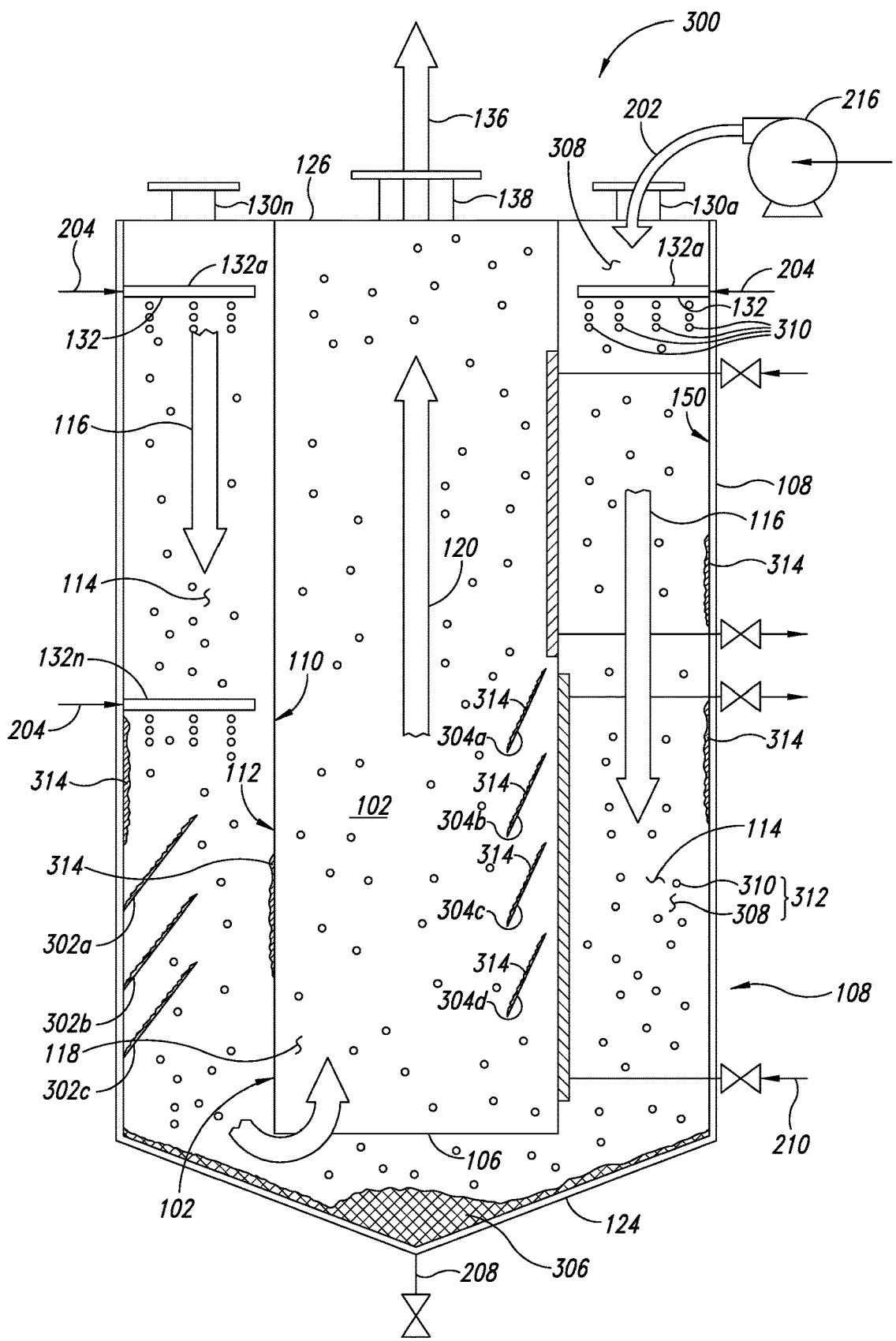
FIG. 3 shows a sectional view of an example fermentor including a single hollow fluid conduit disposed within a surrounding vessel to form downward flow path and upward flow path and an externally mounted fluid mover that forces a flow through both the downward flow path and the upward flow path, according to one or more illustrated embodiments.

FIG. 3 shows a cross-sectional elevation view of an example fermentor 300. The fermentor 300 includes one or more internal structures including one or more structures 302a-302c (only three shown, any number possible, collectively "structures 302") disposed at least partially within the downward flow path 114 and one or more structures 304a-

304d (only four shown, any number possible, collectively "structures 304") disposed at least partially within the upward flow path 120. Such structures can advantageously promote in both the downward and upward flow paths 114, 118 mass transfer between the gas bubbles and liquid in the multi-phase mixture and between the multi-phase mixture and the biological organisms. Such structures can advantageously promote uniformity of gas bubbles within the multi-phase mixture by facilitating a more even distribution within the downward and upward flow paths 114, 118, and promote additional contact time between the gas substrate bubbles present in the multi-phase mixture and the biological organisms within the fermenter 300. The fermentor 300 has a conical bottom 124 that advantageously promotes the collection of excess biomass 306 at a location in the fermentor 300 proximate the at least one biomass removal fluid connection 208.

The fermentor 300 includes one hollow fluid conduit 102 disposed within a vessel 108. The at least one fluid mover 216 is disposed on the inlet side of the downward flow path 114, with liquid flow distributed throughout the downward flow paths 114 in the fermentor 300 via a plurality of fluid connections 130a-130n (collectively, "fluid connections 130") disposed about the top 126 of the fermentor 300. The fluid connections 130 are directly, fluidly, coupled to at least a portion of the downward flow paths 114. The at least one fluid mover 216 provides a generally downward flow 116 of liquid 308 within the downward flow path 114.

The fermentor 300 includes a number of gas distributors 132a-132n (collectively, "gas distributors 132") disposed about the fermentor 300. One or more substrate gases 204 are introduced to the downward flow path 114 in the form of gas bubbles 310. In at least some instances, the gas bubbles 310 can include one or more gas substrates. Within the downward flow path 114, the liquid 308 and the gas bubbles 310 mix and otherwise combine to form the multi-phase mixture 312. Within the downward flow path 114, the gas substrate and nutrients in the multi-phase mixture are used by the biological organisms to form a biomass 314 on most if not all of the internal surfaces forming the downward flow path 114.

In at least some instances, the liquid 308 introduced to the downward flow path 114 can include an aqueous solution containing one or more nutrients, trace elements, minerals, and the like that are capable of supporting the growth and development of a biomass at least within the downward flow path 114. In at least some instances, the liquid 308 can include dissolved nitrogen or one or more nitrogen containing compounds capable of providing a dissolved nitrogen concentration of from about 1 milligram/liter (mg/l) to about 30 mg/l; from about 1 milligram/liter (mg/l) to about 20 mg/l; or from about 1 milligram/liter (mg/l) to about 10 mg/l. In at least some instances, the liquid 308 can include dissolved phosphorous or one or more phosphorous containing compounds capable of providing a dissolved phosphorous concentration of from about 1 mg/l to about 30 mg/l; from about 1 milligram/liter (mg/l) to about 20 mg/l; or from about 1 milligram/liter (mg/l) to about 10 mg/l.

In at least some instances, the gas introduced to the downward flow path 114 can include any number of substrate gases including, but not limited to, at least one of methane, carbon monoxide, oxygen, oxygen containing compounds, hydrogen and hydrogen containing compounds. In at least some instances, the gas(es) may be supplied at conditions (e.g., concentration, temperature and pressure) that advantageously support the dissolution of the gases in the liquid 308 to form the multi-phase mixture 312. In at least some instances, the addition of the substrate gases may be manually or automatically controlled to maintain any defined level of dissolved gas in the multi-phase mixture within the fermentor 300. In some instances, although not shown in FIG. 3, the gas bubbles 310 may be introduced within the downward flow path 114, the upward flow path 120, or both. The gas bubbles 310 introduced at different points in the fermentor 300 may or may not have the same composition or be at the same temperature or pressure. In at least some instances, the composition of the gas bubbles 310 may be adjusted based at least in part on the location within the fermentor 300 at which the gas bubbles 310 are introduced. For example, the substrate gas may have differing concentrations in gas bubbles 310 introduced via one or more gas distributors 132 at various points in the fermentor 300. In at least some instances, the temperature of the gas bubbles 310 may be adjusted based at least in part on the location within the fermentor 300 at which the gas bubbles 310 are introduced. In at least some instances, the pressure of the gas bubbles 310 may be adjusted based at least in part on the location within the fermentor 300 at which the gas bubbles 310 are introduced.

In at least some instances, at least one of the composition, temperature, or pressure of the gas bubbles 310 may be adjusted or otherwise controlled to maintain a dissolved methane concentration within the multi-phase mixture of from about 0.1 mg/l to about 100 mg/l; from about 0.5 mg/l to about 50 mg/l; from about 1 mg/l to about 20 mg/l; or from about 1 mg/l to about 10 mg/l. In at least some instances, at least one of the composition, temperature, or pressure of the gas bubbles 310 may be adjusted or otherwise controlled to maintain a dissolved carbon monoxide concentration within the multi-phase mixture of from about 0.1 mg/l to about 100 mg/l; from about 0.5 mg/l to about 50 mg/l; from about 1 mg/l to about 20 mg/l; or from about 1 mg/l to about 10 mg/l. In at least some instances, at least one of the composition, temperature, or pressure of the gas bubbles 310 may be adjusted or otherwise controlled to maintain a dissolved oxygen concentration within the multi-phase mixture of from about 0.1 mg/l to about 100 mg/l; from about 0.5 mg/l to about 50 mg/l; from about 1 mg/l to about 20 mg/l; or from about 1 mg/l to about 10 mg/l. In at least some instances, at least one of the composition, temperature, or pressure of the gas bubbles 310 may be adjusted or otherwise controlled to maintain a dissolved hydrogen concentration within the multi-phase mixture of from about 0.1 mg/l to about 50 mg/l; from about 0.5 mg/l to about 25 mg/l; from about 1 mg/l to about 10 mg/l; or from about 1 mg/l to about 5 mg/l.

In at least some instances, the structures 302 may be disposed at least partially within the downward flow path 114. Although the gas bubbles 310 would ordinarily tend to flow upward within the downward flow path 114, the fluid velocity within the downward flow path tends to "push" the substrate gas bubbles 310 downward at a velocity that is less than the fluid velocity. The extended residence time of the gas bubbles 310 in the downward flow path 114 advantageously provides an extended opportunity for the gas(es) present in the gas bubbles 310 to dissolve into the multi-phase mixture and consequently for the biological organisms existent in the biomass 314 in the downward flow path 114 to absorb the dissolved substrate gas(es) from the multi-phase mixture. The structures 302 may advantageously enhance this effect as gas bubbles 310 trapped beneath and around the structures will also experience the previously elaborated attendant benefits from an extended residence time within the downward flow path 114. The extended residence time is particularly advantageous in supporting the development of larger quantities of biomass 314 within the downward flow path. The larger quantities of biomass 314 so developed may be at least partially attributable to the enhanced levels of dissolved substrate gas(es) present in the downward flow path 114.

The structures 302 can include any number, type, size, or configuration of projecting member on or recessed detent in fluid contact with the downward flow path 114. All or a portion of the structures 302 can be similar or different dependent upon the function of the structure 302. For example, a number structures 302a sharing a common first design type that promotes mixing of the multi-phase mixture and increases the residence time of the gas bubbles 310 may be disposed within the downward flow path 114. A number of structures 302b sharing a common second design type providing extended surfaces that promote the growth or formation of biomass 314 may be disposed within the downward flow path 114.

In at least some instances, the structures 304 may be disposed at least partially within the upward flow path 120. Although the gas bubbles 310 would flow upward within the upward flow path 114, additional upward velocity is imparted to the gas bubbles 310 by the velocity of the upward fluid flow 120 within the upward flow path 118 which tends to "push" the gas bubbles 310 upward at a velocity that exceeds the normal rise rate of the gas bubbles 310. The structures 304 can advantageously hinder or otherwise impede the progress of the gas bubbles 310 in the upward flow path 118, thereby increasing the residence time of the gas bubbles 310 within the upward flow path 118. The extended residence time of the gas bubbles 310 in the upward flow path 118 advantageously provides an extended opportunity for the gas(es) present in the gas bubbles 310 to dissolve into the multi-phase mixture and consequently for the biological organisms existent in the biomass 314 in the upward flow path 118 to absorb the dissolved substrate gas(es) from the multi-phase mixture. The structures 304 may advantageously enhance this effect as gas bubbles 310 trapped beneath and around the structures 304 will also experience the previously elaborated attendant benefits from an extended residence time within the upward flow path 118. The extended residence time is particularly advantageous in supporting the development of larger quantities of biomass 314 within the upward flow path 118. The larger quantities of biomass 314 so developed may be at least partially attributable to the enhanced levels of dissolved substrate gas(es) present in the upward flow path 118.

The structures 304 can include any number, type, size, or configuration of projecting member on or recessed detent in fluid contact with the upward flow path 118. All or a portion of the structures 304 can be similar or different dependent upon the function of the structure. For example, a number structures 304a sharing a common first design type that promotes mixing of the multi-phase mixture and increases the residence time of the gas bubbles 310 may be disposed within the upward flow path 118. A number of structures 304b sharing a common second design type providing extended surfaces that promote the growth or formation of biomass 314 may be disposed within the upward flow path 114.

As biomass 314 accumulates within the downward flow path 114 and the upward flow path 118, excess biomass will slough or otherwise detach from the interior surfaces of the fermentor 300. At least a portion of the excess biomass will fall to the bottom on the fermentor 300 where the biomass will accumulate. At least a portion of the excess biomass will be carried or transported from the fermentor 300 with the multi-phase mixture 136. Excess biomass accumulations within the bottom of the fermentor 300 may be removed as biosolids. At least a portion of such biosolids may be further processed to yield one or more fungible products such as biofuels or $C_{2+}$ hydrocarbons useful as either finished products or as raw materials for subsequent processing. At least a portion of the excess biomass removed from the fermentor 300 may be used to "re-seed" or propagate the microbiological organisms present in the biosolids in other fermentors 300.

At least a portion of the excess biomass carried from the fermentor 300 with the multi-phase mixture 136 may be separated, for example in the separation subsystem 250, and at least a portion recycled to the fermentor 300 at least to assist in establishing the microbiological colony within the fermentor 300.

In at least some instances, the microbiological organisms used to ferment gaseous carbon-containing feedstocks employ a culture primarily comprising a $C_1$ metabolizing non-photosynthetic microorganism. Such fermentation systems may use one or more species of $C_1$ metabolizing microorganisms that are prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas*, or *Pseudomonas*. In some instances, the $C_1$ metabolizing bacteria may include a methanotroph or a methylotroph. Preferred methanotrophs include *Methylomonas, Methylobacter, Methylococcus, Methylosinus, Methylocystis, Methylomicrobium, Methanomonas*, or a combination thereof. Exemplary methanotrophs include *Methylomonas* sp. 16a (ATCC PTA 2402), *Methylosinus trichosporium* (NRRL B-11,196), *Methylosinus sporium* (NRRL B-11, 197), *Methylocystis parvus* (NRRL B-11, 198), *Methylomonas methanica* (NRRL B-5 11,199), *Methylomonas albus* (NRRL B-11,200), *Methylobacter capsulatus* (NRRL B-11,201), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylosinus trichosporium* OB3b, *Methylococcus capsulatus* Bath, *Methylomonas* sp. 16a, *Methylomicrobium alcaliphilum* 20Z, or a high growth variants thereof. Preferred methylotrophs include *Methylobacterium extorquens, Methylobacterium radiotolerans, Methylobacterium populi, Methylobacterium chloromethanicum, Methylobacterium nodulans*, or a combination thereof.

Microorganisms capable of metabolizing $C_1$ compounds found in syngas include, but are not limited to *Clostridium, Moorella, Pyrococcus, Eubacterium, Desulfobacterium, Carboxydothermus, Acetogenium, Acetobacterium, Acetoanaerobium, Butyribaceterium, Peptostreptococcus*, or combinations thereof may also be used. Exemplary methylotrophs include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or a combination thereof. In some instances, $C_1$ metabolizing microorganisms are eukaryotes such as yeast, including *Candida, Yarrowia, Hansenula, Pichia, Torulopsis*, or *Rhodotorula*.

In other instances, the $C_1$ metabolizing non-photosynthetic microorganism is an obligate $C_1$ metabolizing non-photosynthetic microorganism, such as an obligate methanotroph or methylotroph. In some instances, the $C_1$ metabolizing non-photosynthetic microorganism is a recombinant microorganism comprising a heterologous polynucleotide encoding a fatty acid producing enzyme, a formaldehyde assimilation enzyme, or a combination thereof.

Figure 4:
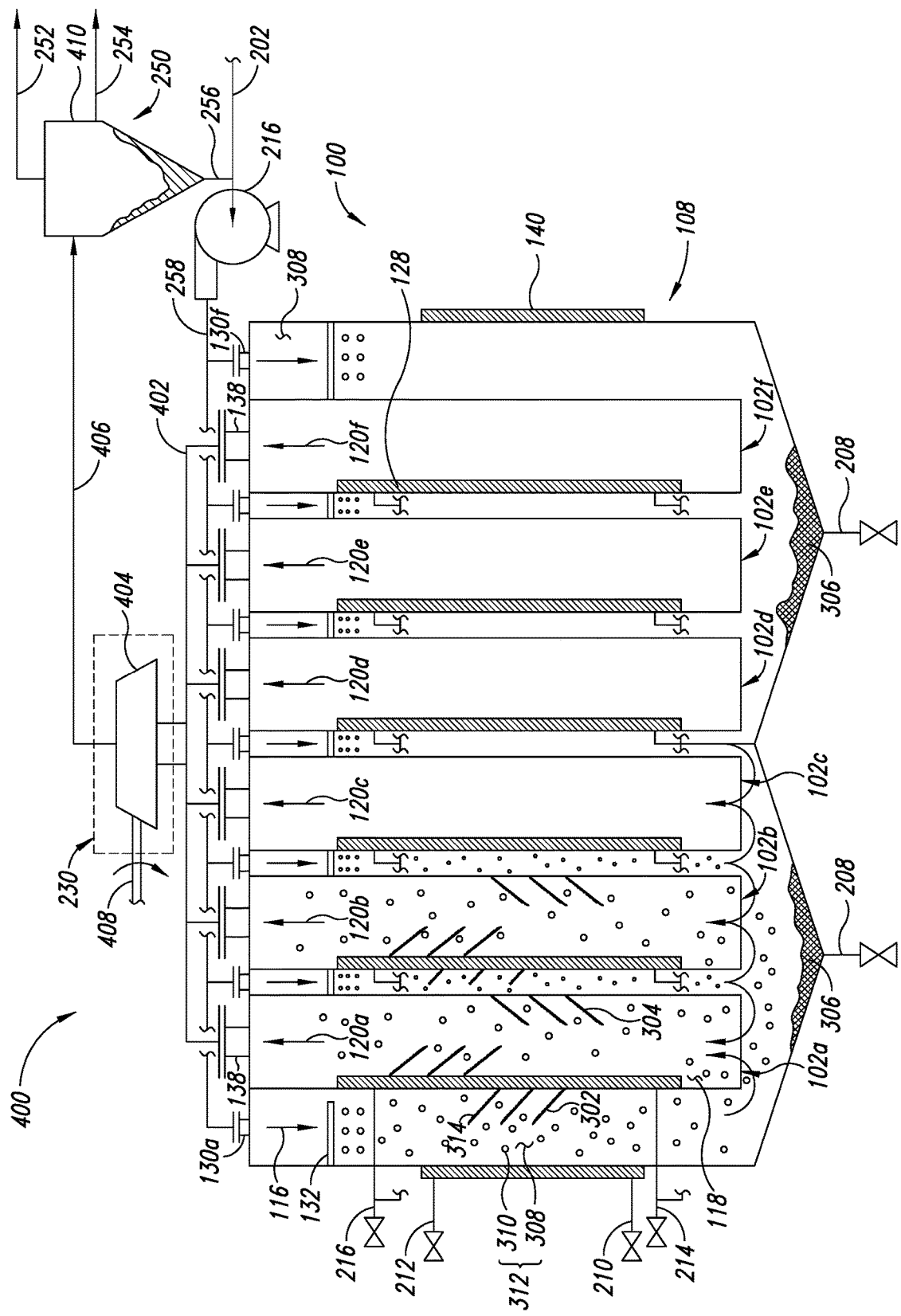
FIG. 4 shows a sectional view of an example fermentor including a number of hollow fluid conduits at least partially surrounded by a vessel to form a number of downward flow paths and upward flow paths and an externally mounted fluid mover that forces a flow through both the downward flow path and the upward flow path, according to one or more illustrated embodiments.

FIG. 4 shows a cross-sectional elevation view of an example fermentor 400. The bottom 124 of the fermentor 400 includes a plurality of conical sections, each of which can accumulate excess biomass 306. In such instances, at least one biomass removal fluid connection 208 can be disposed proximate to the location on the bottom 124 at which the excess biomass accumulates to facilitate the removal of the excess biomass 306. The fermentor 400 includes six or more hollow fluid conduits 102a-102f (collectively, "hollow fluid conduits 102") disposed within the vessel 108. At least one fluid mover 216 is disposed on the inlet side of the downward flow path 114, with liquid flow distributed throughout the downward flow paths 114 via a plurality of fluid connections 130a-130f (collectively, "fluid connections 130") disposed about the fermentor top 126. Each of the fluid connections 130 is directly, fluidly, coupled to the downward flow path 114. The at least one fluid mover 216 provides a generally downward flow of liquid 308 within the downward flow path 114.

The multi-phase mixture 136 exits the fermentor 400 via a plurality of multi-phase mixture discharge fluid connections 138, each of the multi-phase mixture discharge fluid connections directly fluidly coupled to the upward flow paths 118. Each of the multi-phase mixture discharge fluid connections 138 is fluidly coupled to a multi-phase mixture discharge fluid conduit 402 that is used to convey the multi-phase mixture from the upward flow paths 118 to the backpressure subsystem 230.

The backpressure subsystem 230 shown in FIG. 4 includes at least one multi-phase turbine 404. The pressure of the relatively higher pressure multi-phase mixture removed from the upward flow paths 118 is reduced through the multi-phase turbine 404 to provide a relatively lower pressure multi-phase mixture that is directed away from the backpressure system 230 via one or more fluid conduits 406. At least a portion of the relatively lower pressure multi-phase mixture can be subsequently introduced to the separation subsystem 250. In at least some instances, the multi-phase turbine 404 may be physically coupled to one or more energy recovery devices (not shown in FIG. 4) such as an electrical generator to recover at least a portion of the energy released by reducing the pressure of the multi-phase mixture from the relatively higher pressure to the relatively lower pressure. In at least some instances, the physical coupling of the multi-phase turbine 404 and the energy recovery device may be accomplished using a shaft 408 or similar connection capable of transferring mechanical power. The backpressure subsystem 230 can reduce or lower the pressure of the multi-phase mixture exiting the upward flow paths 118 by about 120 psig or less; about 90 psig or less; about 60 psig or less; about 30 psig or less; or about 15 psig or less.

The relatively lower pressure multi-phase mixture exiting the backpressure subsystem 230 via the one or more fluid conduits 406 can in some instances be introduced to the separation subsystem 250. Within the separation subsystem 250, the relatively lower pressure multi-phase mixture can be separated into a plurality of phases. In some instances, the relatively lower pressure multi-phase mixture may be separated at least into a gas phase 252 containing one or more desired products (e.g., $C_{2+}$ hydrocarbons such as ethane and ethylene), one or more unconsumed gas substrates (e.g., methane or carbon monoxide), or one or more metabolic or chemical byproducts (e.g., carbon dioxide). In some instances, the relatively lower pressure multi-phase mixture may be separated at least into a liquid phase 254 containing one or more desired products (e.g., $C_{2+}$ hydrocarbons such as alcohols and ketones) one or more unconsumed liquid phase nutrients, or one or more metabolic or chemical byproducts. In some instances, the relatively lower pressure multi-phase mixture may be separated at least into a solids containing phase 256 containing one or more desired biosolids products (e.g., intracellular lipids useful as a biofuel) or one or more metabolic or chemical byproducts (e.g., excess biomass).

Figure 5:
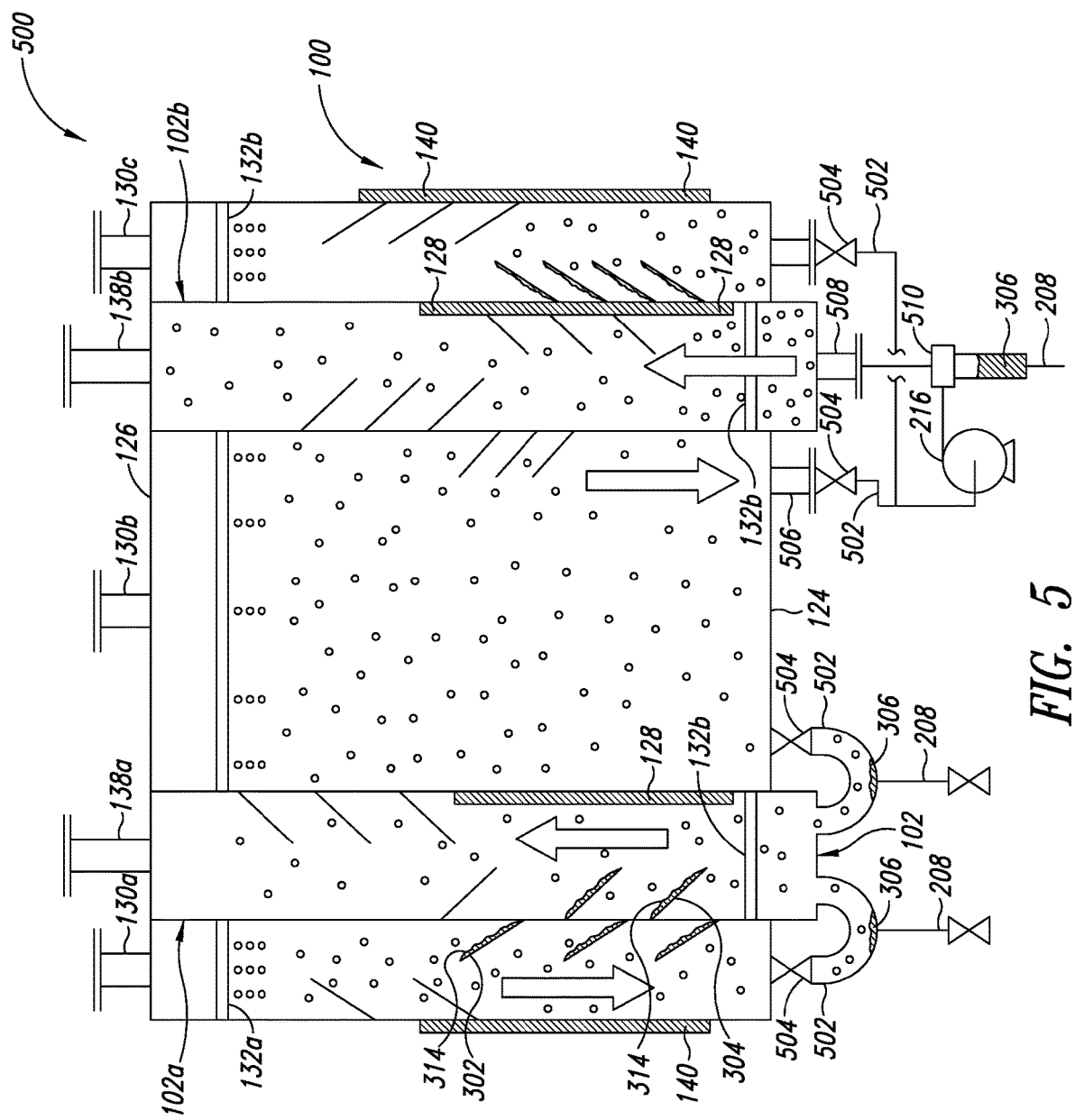
FIG. 5 shows a sectional view of an example fermentor including a number of hollow fluid conduits at least partially surrounded by a vessel to form a number of downward flow paths and upward flow paths and an externally mounted fluid mover that induces a flow through the downward flow path and forces a flow through the upward flow path, according to one or more illustrated embodiments.

FIG. 5 shows a cross-sectional elevation view of an example fermentor system 500. The fermentor 500 includes a plurality of hollow fluid conduits 102 that extend completely through (i.e., from the top 126 to the bottom 124) of the vessel 108. The upward flow paths 118 are fluidly coupled to the downward flow paths 114 via one or more fluid conduits 502. In at least some instances, one or more isolation devices 504 may be disposed in at least a portion of the one or more fluid conduits 502. In at least some instances, the one or more fluid conduits 502 are fluidly coupled to at least a portion of the downward flow paths 114 using one or more fluid connections 506. In at least some instances, the one or more fluid conduits 502 are fluidly coupled to at least a portion of the upward flow paths 118 using one or more fluid connections 508. The one or more isolation devices 504 and the one or more fluid connections 506, 508 advantageously permit the isolation of one or more hollow fluid conduits 102. The ability to selectively isolate the hollow fluid conduits 102 advantageously permits routine maintenance and cleaning of the hollow fluid conduits 102 without requiring the entire fermentor 500 be taken out of service.

Two different systems are shown coupling the downward flow path 114 and the upward flow path 118. In a first instance, fluid conduits 502 are shown directly fluidly coupling the downward flow path 114 and the upward flow path 118. Such a direct fluid coupling installation may be used where the forced fluid flow or induced fluid flow is used in both the downward flow path 114 and the upward flow path 118. For example, a direct fluid coupling system may be advantageous where the one or more fluid movers 216 are fluidly coupled to the inlet fluid connection 130 of the downward flow path 114 or are fluidly coupled to the outlet fluid connection 138 of the upward flow path 118. In this instance, excess biomass 306 can accumulate within the fluid conduits 502. Such accumulated excess biomass 306 may be removed using the at least one biomass removal fluid connection 208.

In a second instance, one or more fluid movers 216 are fluidly coupled between the downward flow path 114 and the upward flow path 118. Such a fluid coupling provides an induced downward flow 116 in the downward flow path 114 and a forced upward flow 120 in the upward flow path 118. In at least some instances, the one or more fluid movers 216 may be fluidly coupled to the downward flow path 114 using one or more fluid connections (e.g., flanged, threaded, quick connect, etc.) 506. In at least some instances, the one or more fluid movers 216 may be fluidly coupled to the upward flow path using one or more fluid connections (e.g., flanged, threaded, quick connect, etc.) 508.

In at least some instances, excess biomass 306 drawn into the one or more fluid movers 216 may be trapped or otherwise accumulated in one or more accumulators 510. Example accumulators 510 include, but are not limited to, one or more single or multi-stage filtration devices such as cartridge filters, self-cleaning filters, bag filters, basket filters, or combinations thereof. Example accumulators 510 can include, but are not limited to, one or more hydrocyclones or the like. In at least some instances, at least a portion of the excess biomass 306 can be removed from the accumulator 510 using the at least one biomass removal fluid connection 208. Although not shown in FIG. 5, in at least some instances, one or more biomass removal fluid connections 208 may be disposed on the vessel 108. For example, one or biomass removal fluid connections 208 may be disposed on the bottom 124 of the vessel 108 to removed accumulated biosolids 306.

The fermenter 500 is also equipped with a plurality of gas distribution headers 132. A first gas distribution header 132a is disposed in the downward flow path 114. A second gas distribution header 132b is disposed in the upward flow path 118. Such an arrangement advantageously provides the ability to replenish or increase a gas substrate depleted from the multi-phase mixture during the passage through the downward flow path 114 prior to the multi-phase mixture entering the upward flow path 118. For example, if methane is being used as a gas substrate, and the methane concentration in the multi-phase mixture exiting the downward flow path is below a defined value, additional methane may be added to the multi-phase mixture in the upward flow path 118 using the gas distribution header 132b. The second gas distribution header 132b may advantageously provide the ability to raise different types of microorganisms at different locations within the fermenter 500. For example, introducing a first gas substrate via the first gas distribution header 132a may promote the growth of first gas substrate metabolizing microorganisms in the downward flow path 114. Introducing a second gas substrate via the second gas distribution header 132b may promote the growth of second gas substrate metabolizing microorganisms in the upward flow path 114. The ability to feed a plurality of gas substrates in the same fermentor 500 may advantageously expand the product matrix achievable in the fermentor 500.

Figure 6:
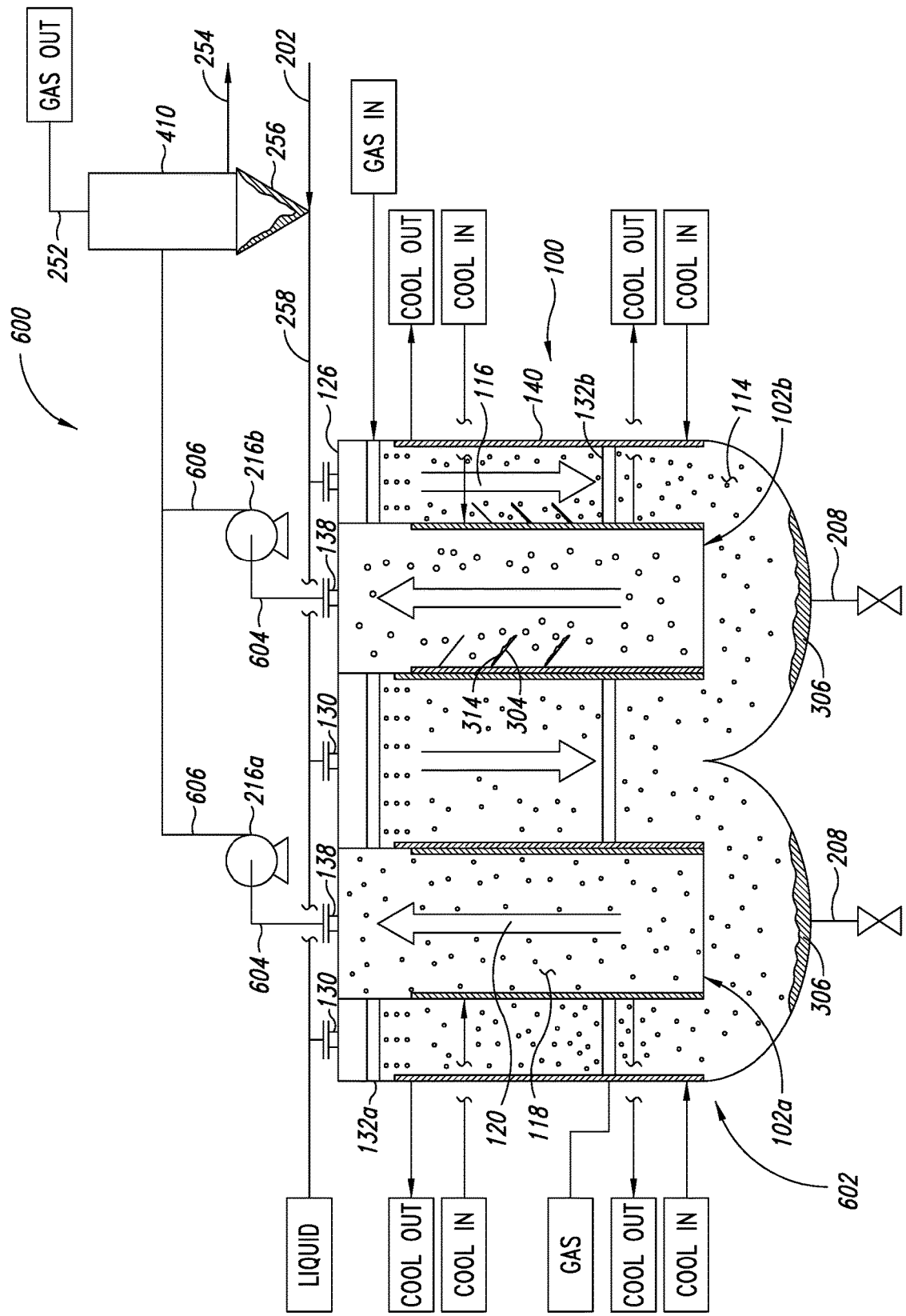
FIG. 6 shows a sectional view of an example fermentor including a number of hollow fluid conduits at least partially surrounded by a dished bottom vessel to form a number of downward and upward flow paths and an externally mounted fluid mover that induces a flow through the downward flow path and forces a flow through the upward flow path, according to one or more illustrated embodiments.

FIG. 6 shows a cross-sectional elevation view of an example fermentor system 600. The bottom of the vessel 108 includes a plurality of dished heads (e.g., ASME dished heads, each of which can accumulate excess biomass 306. In such instances, at least one biomass removal fluid connection 208 can be disposed proximate the location on the bottom 124 at which the excess biomass accumulates to facilitate the removal of the excess biomass 306. The fermentor 602 includes a plurality of hollow fluid conduits 102a-102b (collectively, "hollow fluid conduits 102") disposed within the vessel 108.

At least one fluid mover 216 is fluidly coupled to the upward flow path 118 via one or more multi-phase mixture discharge fluid connections 138. Such an arrangement, where both the downward flow path 114 and the upward flow path 118 are fluidly coupled to the suction side of the at least one fluid mover 216 can at least partially induce a fluid flow through both the downward flow path 114 and the upward flow path 118. Although not shown in FIG. 6, in at least some instances, one or more optional additional fluid movers 216 may be fluidly coupled to the downward flow path 114 via one or more liquid distribution headers 130a-130c. The at least one fluid mover 216 is fluidly coupled to the A plurality of gas distribution headers 132a-132b (collectively "gas distribution headers 132") is in fluid communication with the downward flow path 114 of the fermentor 602. Such an arrangement advantageously provides the ability to replenish or increase a gas substrate depleted from the multi-phase mixture during the passage through the downward flow path 114 prior to the multi-phase mixture entering the upward flow path 118. For example, if methane is being used as a gas substrate, and the methane concentration in the multi-phase mixture exiting the downward flow path is below a defined value, additional methane may be added to the multi-phase mixture in the upward flow path 118 using the gas distribution header 132b. The second gas distribution header 132b may advantageously provide the ability to raise different types of microorganisms at different locations within the fermentor 602. For example, introducing a first gas substrate via the first gas distribution header 132a may promote the growth of first gas substrate metabolizing microorganisms in the downward flow path 114. Introducing a second gas substrate via the second gas distribution header 132b may promote the growth of second gas substrate metabolizing microorganisms in the upward flow path 114. The ability to feed a plurality of gas substrates in the same fermentor 602 may advantageously expand the product matrix achievable in the fermentor 602.

Figure 7:
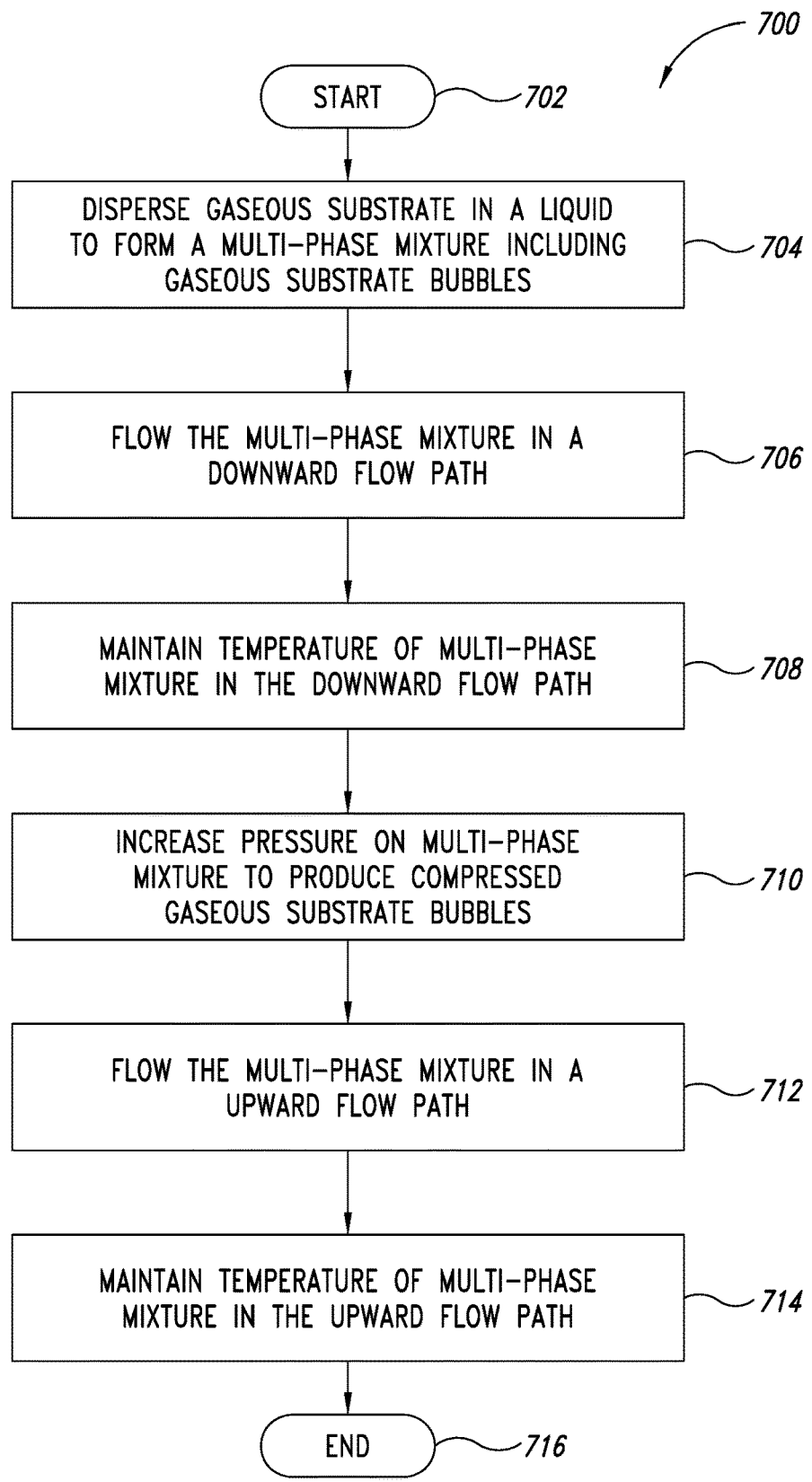
FIG. 7 shows a high level flow diagram of a fermentation method including optional cooling in both the downward and upward flow paths, according to one or more illustrated embodiments.

FIG. 7 shows a high level method of operation of a fermentation system using one or more fermentors 100 in one or more fermentor systems 300, 400, 500, 600 described in detail above with regard to FIGS. 1-6. Such systems advantageously introduce one or more liquid media containing one or more nutrients and one or more gaseous substrates in a downward flow path 114 to provide a multi-phase mixture having an overall downward flow 116 therein. The fluid velocity of the multi-phase mixture within the downward flowpath 114 is sufficient to cause the gas substrate bubbles present in the multi-phase mixture to flow in a downward direction. However, the tendency for the gaseous substrate bubbles to rise within the multi-phase mixture advantageously extends the residence time of the gaseous substrate bubbles within the downward flow path 114, thereby enhancing mass transfer and subsequent microbiological uptake of the gaseous substrate in the downward flow path. After passing through the downward flow path 114, the multi-phase mixture enters the upward flow 118 path where additional mass transfer and microbiological uptake may occur. The multi-phase mixture is removed from the fermentor and optionally pressure reduced and separated to provide one or more desired materials. The method commences at 702.

At 704 the gaseous substrate is dispersed within the liquid media to form the multi-phase mixture. Such dispersion may occur at or near the inlet or beginning of the downward flow path 114, although additional quantities of gaseous substrate may be dispersed at other locations in the downward flow path 114, the upward flow path 118, or both. In some instances, gaseous substrate may be dispersed at multiple points within the downward flow path 114, upward flow path 118, or both and the gaseous substrate at each dispersion point may have the same or a different temperature, pressure, composition, or combinations thereof. The ability to vary physical or compositional properties of the gaseous substrate at different locations within the fermentor advantageously permits the tailoring of the gaseous substrate not only to the specific microbiological species present in the fermentor, but also to the specific location of the microbiological species within the fermentor based on the dispersion point of the gaseous substrate within the fermentor.

At 706 the multi-phase mixture provides a downward flow 116 within the downward flow path 114. The substrate gas bubbles will tend to rise within the downward flow path at a gas bubble rise rate of "X" feet per second. The multi-phase mixture will have a superficial fluid velocity within the downward flow path 114 of "Y" feet per second. By maintaining the superficial fluid velocity of the multiphase mixture above the gas bubble rise rate (i.e., Y>X), the substrate gas bubbles will flow downward rather than upward in the downward flow path 114. By adjusting or otherwise controlling the flow rate of the multi-phase mixture in the downward flow path 114 to a velocity that only slightly exceeds the gas substrate bubble rise rate, the residence time of the gas bubbles in the downward flow path 114 can be increased. Such an increase in residence time in the downward flow path 114 can advantageously improve mass transfer and microbiological uptake of the gas substrate 204 by the microbiological organisms present in the downward flow path 114. In some instances, the velocity of the multi-phase mixture in the downward flow path 114 can be measured and controlled. For example the control subsystem 290 can alter, adjust or control the fluid velocity of the multi-phase mixture in the downward flow path 114 to a defined range slightly in excess of the rise rate of the substrate gas bubbles in the downward flow path 114. In some instances, the temperature, pressure, or composition of the gas substrate 204 may be altered, adjusted or controlled via the control subsystem 290 to maintain a desired gas substrate bubble size within the downward flow path 114. In other instances, the temperature, pressure, or composition of the gas substrate 204 may be altered, adjusted or controlled via the control subsystem 290 to maintain the concentration of one or more gas substrate components (e.g., methane, carbon dioxide, hydrogen, oxygen, nitrogen, etc.) within the liquid phase of the multi-phase mixture in a defined range in the downward flow path 114.

At 708 the temperature of the multi-phase mixture within the downward flow path 114 can be altered, adjusted, or controlled to maintain the temperature within a defined temperature range. In at least some instances, the defined temperature range may be selected or otherwise chosen based at least in part on the microbiological species used within the fermentor 100. Excess heat may be generated as a byproduct by the microbiological organisms responsible for at least a portion of the activity within the fermentor 100. This excess heat, if left uncontrolled, can inhibit or adversely affect the growth or metabolism of some or all of the microbiological organisms within the fermentor 100. In at least some instances, cooling may be provided within the downward flow path 114 to maintain the temperature of the multi-phase mixture in the downward flow path 114 within a defined range. Such cooling may include passage of a cooling media through reservoirs or coils 140 thermally conductively coupled to the downward flow path 114. Cooling water or other cooling media (e.g., glycol solutions, brine solutions, etc.) may also be used to provide cooling within the fermentor 100. In at least some instances, the control subsystem 290 may control the flow rate or temperature of the cooling media passed through the reservoirs or coils 140 that are thermally conductively coupled to the downward flow path 114.

In other instances, the heat produced by the microbiological species may be insufficient to maintain the fermentor within a desired temperature range. Such may occur, for example, in extremely cold environments where the fermentor 100 is located in an exposed or partially exposed exterior location. In some instances, the reservoirs or coils 140 thermally conductively coupled to the downward flow path 114 used for cooling may also be used or provide warming to the fermentor 100. In other instances, dedicated warming reservoirs or coils may be thermally conductively coupled to the downward flow path 114. Such warming may include passage of a warming media through the reservoirs or coils placed at least partially within the downward flow path 114. Warm water, steam, or similar heat transfer fluids (e.g., glycol solutions, thermal oils, etc.) may also be used to optionally provide warming within the fermentor 100. In at least some instances, the control subsystem 290 may control the flow rate or temperature of the warming media passed through the reservoirs or coils 140 that are thermally conductively coupled to the downward flow path 114.

At 710, the pressure on the gas substrate bubbles traveling with the multi-phase mixture in the downward flow 116 within the downward flow path 114 will increase as the gas substrate bubbles are pushed deeper along the downward flow path. The pressure increase may be at least partially attributable to the increase in hydrostatic pressure exerted on the gas substrate bubbles by the column of liquid in the fermentor 100. The pressure increase can, in some instances, advantageously increase the mass transfer between the gas substrate bubbles and the liquid media forming the multi-phase mixture in the downward flow path 114. In at least some instances, the increased pressure on the gas substrate bubbles may also advantageously improve the uptake of one or more components present in the gas substrate by the microbiological organisms present in the downward flow path.

At 712, the multi-phase mixture exits the downward flow path and enters the upward flow path 118. The multi-phase mixture entering the upward flow path can include, but is not limited to the liquid containing unabsorbed nutrients, the gas substrate bubbles containing undissolved and unabsorbed gas substrate. The multi-phase mixture entering the upward flow path 118 may also contain entrained biological matter swept from the walls and/or floor of the fermentor 100. In at least some instances, one or more structures promoting mass transfer may be disposed within at least a portion of the upward flow path 118. Such structures may include, but are not limited to, one or more baffles, one or more unpowered or static mixers, one or more powered or dynamic mixers, and the like. In at least some instances, additional liquid containing one or more nutrients or additional gas substrate may be introduced to the upward flow path 118. Such additional nutrients or gas substrates may be introduced to replenish those consumed via chemical or microbiological processes in the downward flow path 118. Such additional nutrients or gas substrates may be introduced to provide additional or different nutrients or gas substrates to the microbiological organisms present in the upward flow path 118. As the multi-phase mixture flows upward 120, pressure on the gas substrate bubbles present in the multi-phase mixture will gradually lessen as the hydrostatic head decreases on the rise through the upwards flow path 118.

At 714, the temperature of the multi-phase mixture within the upward flow path 118 can be altered, adjusted, or controlled to maintain the temperature within a defined temperature range. In at least some instances, the defined temperature range may be selected or otherwise chosen based at least in part on the microbiological species used within the fermentor 100. Excess heat may be generated as a byproduct by the microbiological organisms responsible for at least a portion of the activity within the fermentor 100. This excess heat, if left uncontrolled, can inhibit or adversely affect the growth or metabolism of some or all of the microbiological organisms within the fermentor 100. In at least some instances, cooling may be provided within the upward flow path 118 to maintain the temperature of the multi-phase mixture in the upward flow path 118 within a defined range. Such cooling may include passage of a cooling media through reservoirs or coils 128 thermally conductively coupled to the upward flow path 118. Cooling water or other cooling media (e.g., glycol solutions, brine solutions, etc.) may also be used to provide cooling within the fermentor 100. In at least some instances, the control subsystem 290 may control the flow rate or temperature of the cooling media passed through the reservoirs or coils 128 thermally conductively coupled to the upward flow path 118.

In other instances, the heat produced by the microbiological species may be insufficient to maintain the fermentor within a desired temperature range. Such may occur, for example, in extremely cold environments where the fermentor 100 is located in an exposed or partially exposed exterior location. In some instances, the reservoirs or coils 128 thermally conductively coupled to the upward flow path 118 used for cooling may also be used or provide warming to the fermentor 100. In other instances, dedicated warming reservoirs or coils may be thermally conductively coupled to the upward flow path 118. Such warming may include passage of a warming media through the reservoirs or coils placed at least partially within the upward flow path 118. Warm water, steam, or similar heat transfer fluids (e.g., glycol solutions, thermal oils, etc.) may also be used to optionally provide warming within the fermentor 100. In at least some instances, the control subsystem 290 may control the flow rate or temperature of the warming media passed through the reservoirs or coils 128 that are thermally conductively coupled to the upward flow path 118. The process concludes at 716.

Figure 8:
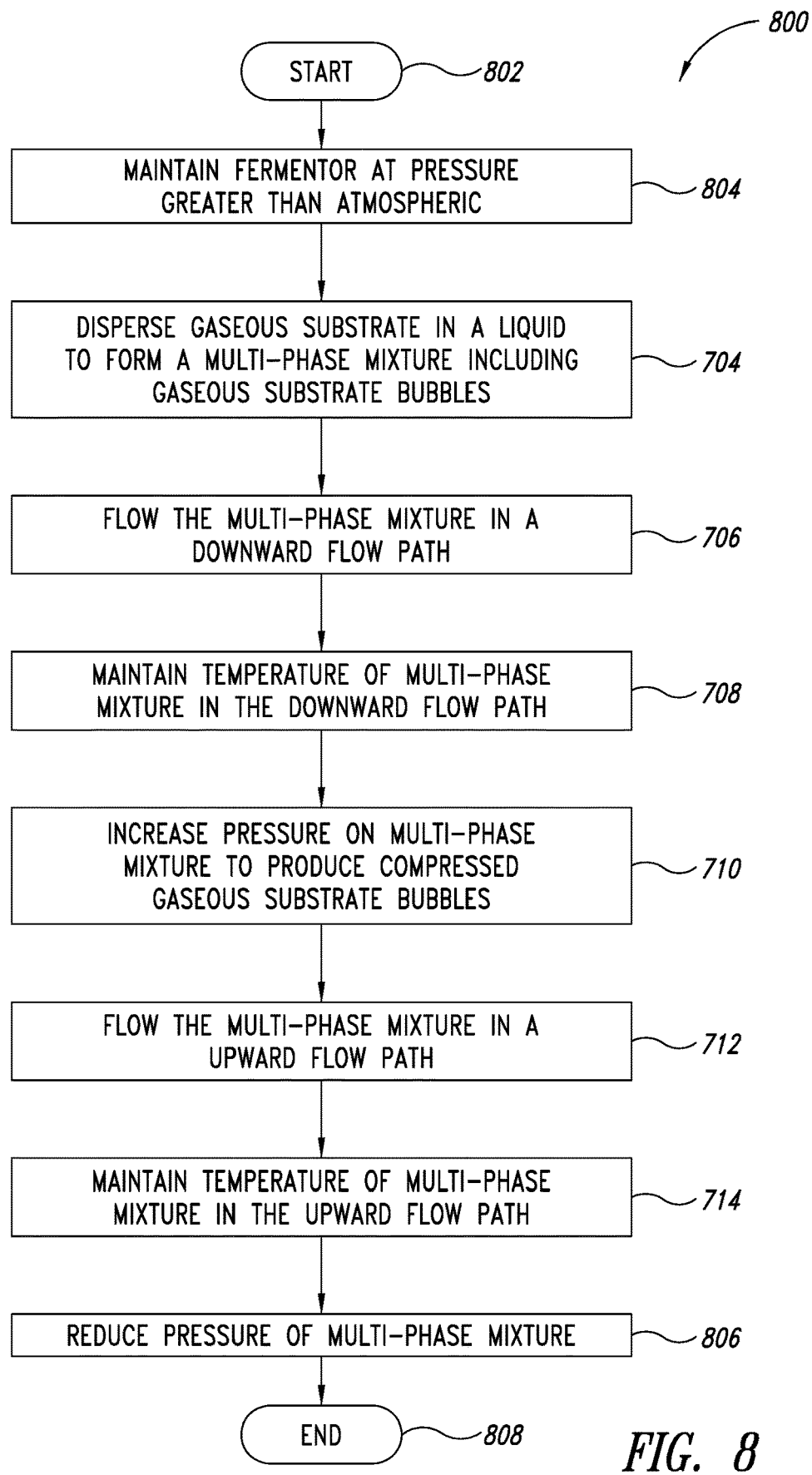
FIG. 8 shows a high level flow diagram of a fermentation method that includes optionally holding the fermentor at an elevated pressure using a backpressure subsystem, according to one or more illustrated embodiments.

FIG. 8 shows a high level method of operation 800 of a fermentation system using one or more fermentors 100 in one or more fermentor systems 300, 400, 500, 600 described in detail above with regard to FIGS. 1-6. The example fermentation method 800 uses the identical or nearly identical steps to those described in detail with regard to the fermentation method 700 discussed in detail in FIG. 7, with the exception that the fermentation method 800 is conducted at an elevated pressure using one or more backpressure subsystems 230. Such backpressure subsystems 230 advantageously maintain the pressure in the fermentor 100 at a level greater than atmospheric pressure, thereby increasing the partial pressure of the gas(es) contained in the gas bubbles 310 in the multi-phase mixture 312. By increasing the partial pressure of the gas(es) within the gas bubbles 310, the mass transfer rate between the gas bubbles 310 and the liquid 308 is enhanced and the increased availability of the dissolved gas(es) within the multi-phase mixture beneficially improves the uptake of the gas(es) by the microbiological organisms in the fermentor 100. The method commences at 802.

At 804 the liquid 308 and the gas(es) are introduced to the fermentor 100 at a first pressure that is greater than atmospheric pressure. The presence of the backpressure subsystem 230 maintains the pressure within the fermentor 100, thereby increasing the pressure in both the downward flow path 114 and the upward flow path 118. In at least some instances, the first pressure can be from about 5 psig to about 150 psig; from about 5 psig to about 100 psig; or from about 5 psig to about 75 psig. As the multi-phase mixture passes through the downward flow path 114, the hydrostatic pressure will build on the gas bubbles 310 further increasing the partial pressure of the gas(es) present in the gas bubbles 310 and further increasing the mass transfer rate between the gas bubbles 310 and the multi-phase mixture. The pressure of the multi-phase mixture will increase to a second pressure at the bottom of the downward flow path 118. In at least some instances, the second pressure can be from about 10 psig to about 150 psig; from about 10 psig to about 100 psig; or from about 10 psig to about 75 psig. As the multi-phase mixture passes through the upward flow path 118, the hydrostatic pressure on the gas bubbles 310 will be relieved to a third pressure at the exit of the upward flow path 118. In at least some instances, the third pressure can be from about 5 psig to about 150 psig; from about 5 psig to about 100 psig; or from about 5 psig to about 75 psig.

At 806 the multi-phase mixture exiting the hollow fluid conduits via the multi-phase mixture discharge fluid connection 138 is directed to the backpressure subsystem 230. Within the backpressure subsystem 230, one or more systems or devices are used to reduce the pressure of the multi-phase mixture to a level that is less than the third pressure. Such pressure reduction may be accomplished using one or more pressure drop inducing devices such as an orifice plate or a backpressure control valve. In one or more instances, the one or more pressure drop inducing devices can include a multi-phase turbine through which the high pressure multi-phase mixture is passed to provide the low pressure multi-phase mixture 232 at a fourth pressure. In at least some instances, the fourth pressure can be from about 5 psig to about 150 psig; from about 5 psig to about 100 psig; or from about 5 psig to about 75 psig. In at least some instances, at least a portion of energy released during the reduction in pressure of the multi-phase mixture 136 may be captured, for example the energy released in the multi-phase turbine may be used to turn an electrical generator, fluid mover, or gas mover. The method concludes at 808.

Figure 9:
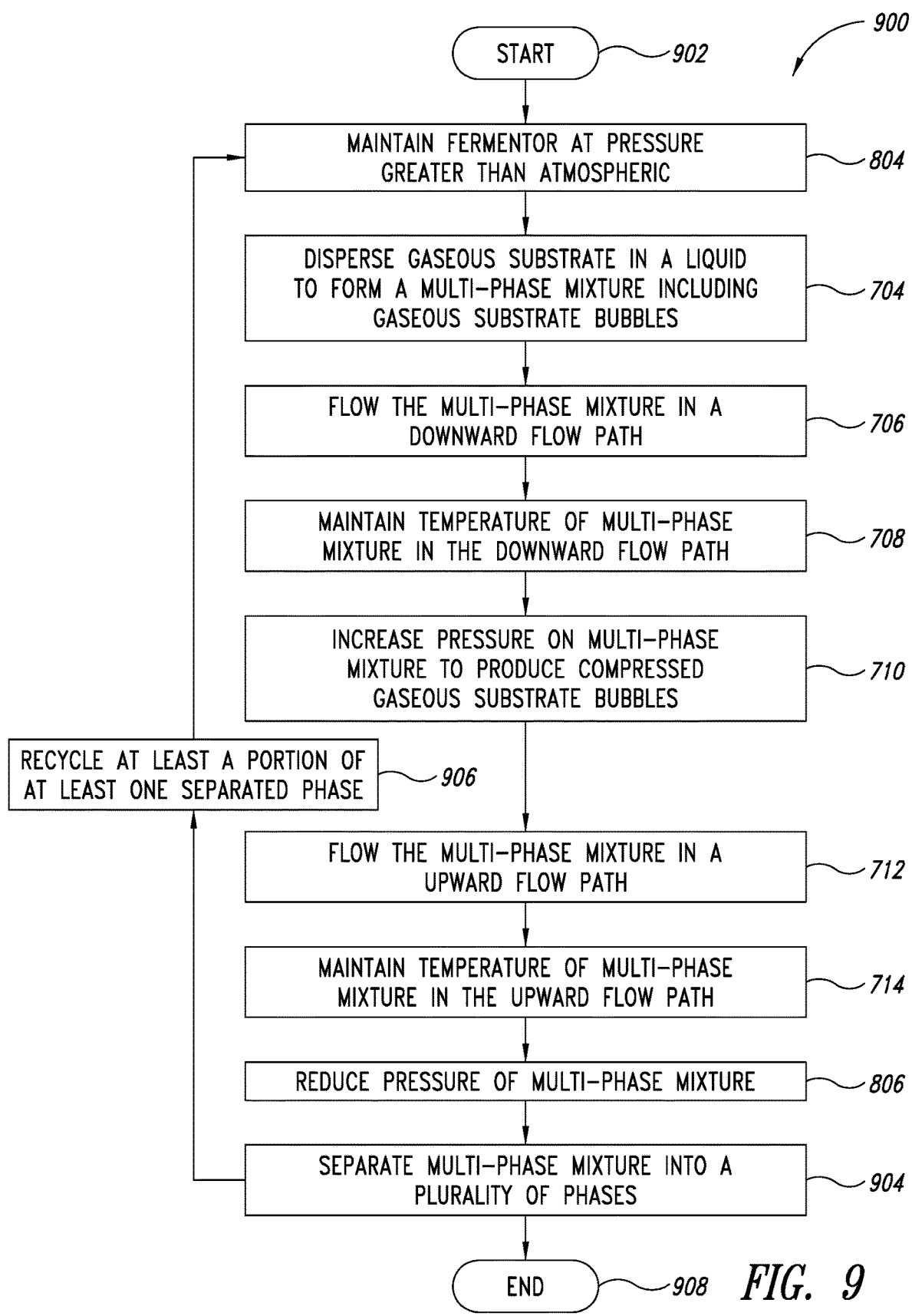
FIG. 9 shows a high level flow diagram of a fermentation method that includes optionally holding the fermentor at an elevated pressure using a backpressure subsystem, separating the multi-phase mixture removed from the fermentor in an optional separation subsystem, and recycling at least a portion of the separated multi-phase mixture back to the fermentor according to one or more illustrated embodiments.

FIG. 9 shows a high level method of operation 900 of a fermentation system using one or more fermentors 100 in one or more fermentor systems 300, 400, 500, 600 described in detail above with regard to FIGS. 1-6. The example fermentation method 900 employs an identical or nearly identical method to the fermentation methods 700 and 800 discussed in detail with regard to FIG. 7 and FIG. 8, with the exception that the low pressure multi-phase mixture 232 removed from the backpressure subsystem 230 is introduced to and separated in a separation subsystem 250. The separation subsystem 250 can include one or more devices or systems to separate the low pressure multi-phase mixture into at least a gas and a liquid. In some instances, the separation subsystem 250 may separate the low pressure multi-phase mixture 232 into a gas 252, a liquid 254, and a solids-rich liquid 256. The method commences at 902.

At 904, the low pressure multi-phase mixture 232 from the separation subsystem 230 is introduced to the separation subsystem 250. Within the separation subsystem the multi-phase mixture 232 can be separated into at least a gas 252 and a liquid 254. In at least some instances, at least a portion of the separated gas 252 may be subsequently processed or separated. At least a portion of the processed or separated gas may be recycled to the fermentor 100 as a gas substrate 204. In some instances, at least a portion of the separated gas may be sold or otherwise disposed. In at least some instances, at least a portion of the separated gas may be sold or traded as a fungible commodity. In at least some instances, the separated gas may include one or more $C_{2+}$ hydrocarbon gases, including but not limited to, ethane, ethylene, propane, butane, and compounds thereof.

In at least some instances, at least a portion of the separated liquid 254 may be subsequently processed or separated. At least a portion of the separated gas 252 may be subsequently processed or separated. At 906 at least a portion of the processed or separated liquid which may or may not include biosolids removed from the fermentor 100 with the multi-phase mixture 136 can be recycled to the fermentor 100. For example, at least a portion of the separated liquid 256 containing biosolids may be combined with at least a portion of the liquid feed 202 to provide the mixture 258 fed to the fermentor 100. Such recycle may advantageously provide an ongoing, continuous or semi-continuous, inoculation of the fermentor 100 with established biological species. In some instances, at least a portion of the separated liquid may be sold or otherwise disposed. In at least some instances, at least a portion of the separated liquid may be sold or traded as a fungible commodity. In at least some instances, the separated liquid may include one or more $C_{2+}$ hydrocarbon liquids, including but not limited to one or more alcohols, glycols, or ketones. The process concludes at 908.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other fermentors and fermentation systems. Such fermentors and fermentation systems may include fermentors for purposes other than chemical intermediate production, and may include fermentors and fermentation systems useful in food or beverage production. Similarly, the ancillary systems described herein, including the cooling subsystem, the backpressure subsystem, the separation subsystem, and the control subsystem may include a single system, for example a package cooling tower or package control system, or may include a custom designed subsystem including any number of subcomponents that are physically, fluidly, and communicably coupled in a manner facilitating the controlled production and distribution of cooling or warming media (i.e., by the cooling subsystem); facilitating the controlled maintenance of backpressure on the fermentor system with or without the supplemental generation of energy (i.e., by the backpressure subsystem); facilitating the separation of at least a portion of the multi-phase mixture into a gas, liquid, and semi-solid for recycle or for recovery and subsequent processing or sale (i.e., by the separation subsystem). The control subsystem can include an integrated or distributed control system that provides monitoring, alarming, control, and control output for all or a portion of the fermentation system or any of the ancillary subsystems. The control subsystem may also include any number of individual loop controllers and the like for control of one or more aspects of the fermentation system or any of the ancillary subsystems.

The foregoing detailed description has set forth various embodiments of the devices and/or processes via the use of process flow diagrams, equipment sectional views, and example methods. Insofar as such block diagrams, schematics, and examples contain one or more functions and/or operations, it will be understood by those skilled in the art that each function and/or operation within such block diagrams, flowcharts, or examples can be implemented, individually and/or collectively, using wide range of off-the-shelf or customized components that are well known to those of skill in the chemical engineering arts. For example, although only circular, triangular, and square hollow metal conduits are explicitly discussed, one of skill in the art would realize that virtually any hollow fluid conduit could be substituted. The microbiological species listed herein are intended to provide a sample of the potential microbiological species that can be supported in a fermentor or fermentor system as described herein.

The various embodiments described above can be combined to provide further embodiments. All U.S. patents, U.S. patent application publications, U.S. patent applications, foreign patents, foreign patent applications and non-patent publications referred to in this specification and/or listed in the Application Data Sheet, including but not limited to, U.S. Provisional Patent Application Ser. No. 61/671,542, filed Jul. 13, 2012, U.S. Provisional Patent Application Ser. No. 61/711,104, filed Oct. 8, 2012, International PCT Application No. PCT/US2013/063650, filed Oct. 7, 2013 and U.S. Non-Provisional application Ser. No. 14/434,315, filed Apr. 8, 2015, are incorporated herein in their entirety. Aspects of the embodiments can be modified, if necessary, to employ systems, processes, biological media, and concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for producing $C_4$ compounds, the method comprising culturing a methanotroph comprising a heterologous polynucleotide on a $C_1$ substrate comprising methane in a controlled culturing unit under conditions sufficient for the methanotroph comprising the heterologous polynucleotide to produce one or more of the products crotonic acid or salts thereof, n-butanol, isobutanol, 1,3-butanediol, 1,4-butanediol, and 2,3-butanediol, wherein the methanotroph is a *Methylococcus capsulatus* Bath, *Methylomonas* sp. 16a, *Methylosinus trichosporium* OB3b, *Methylosinus sporium*, *Methylocystis parvus*, *Methylomonas methanica*, *Methylomonas albus*, *Methylobacter capsulatus*, *Methylobacterium organophilum*, *Methylomonas* sp. AJ-3670, *Methylomicrobium alcahphilum*, *Methylocella silvestris*, *Methylacidiphilum infernorum*, *Methylibium petroleiphilum*, or a high growth variants thereof, wherein the culturing in the controlled culturing unit includes:
dispersing the $C_1$ substrate comprising methane in a liquid media including at least water and one or more nutrients to form a multi-phase mixture comprising $C_1$ substrate bubbles dispersed in the liquid media;
flowing at a first velocity and a first pressure the multi-phase mixture in one or more downward flow paths before flowing the multi-phase mixture in a number of upward flow paths each defined by a closed fluid channel, the one or more downward flow paths formed between an exterior perimeter of a number of hollow fluid conduits and an interior perimeter of a vessel at least partially surrounding the number of hollow fluid conduits, the vessel including a top and the number of hollow fluid conduits extending from the top of the vessel;
increasing the pressure of the multi-phase mixture from the first pressure to a second pressure to produce compressed $C_1$ substrate bubbles in the multi-phase mixture while contacting the multi-phase mixture with the methanotrophs present in the one or more downward flow paths to provide a first biomass;
flowing at a second velocity the multi-phase mixture in the number of upward flow paths, each of the respective number of upward flow paths formed by an interior perimeter of each of the number of hollow fluid conduits and maintaining the pressure at or above a third pressure to maintain compressed $C_1$ substrate bubbles in the multi-phase mixture while contacting the multi-phase mixture with the methanotrophs present in the number of upward flow paths to provide a second biomass; and discharging the multi-phase mixture, flowing in the number of upward flow paths, from the vessel to outside the vessel through a top of the vessel without the multi-phase mixture from the upward flow path being recirculated within the vessel to the downward flow path.

2. The method of claim 1, wherein the methanotroph is an obligate methanotroph.

3. The method of claim 1, wherein the methanotroph is *Methylococcus capsulatus* Bath, *Methylosinus trichosporium* OB3b, or *Methylomonas* sp. 16a.

4. The method of claim 1, wherein the methanotrophs are cultured aerobically.

5. The method of claim 1, further comprising maintaining a first temperature in the downward flow path using a thermal transfer system thermally coupled to the downward flow path, thermally coupled to the upward flow path, or both.

6. The method of claim 1, wherein the first velocity exceeds the rise rate of any $C_1$ substrate bubbles present in the multi-phase fluid present in the downward flow path.

7. The method of claim 1, wherein the $C_1$ substrate includes at least one of hydrogen or a hydrogen containing compound, at least one of oxygen or an oxygen containing compound.

8. The method of claim 1, wherein the $C_1$ substrate comprising methane further comprises oxygen.

9. The method of claim 8, wherein the methane feed rate is at least about 5 grams of methane per liter of liquid media (g/l).

10. The method of claim 8, wherein the oxygen feed rate is at least about 5 grams of oxygen per liter of liquid media (g/l).

11. The method of claim 8, wherein the $C_1$ substrate is at a pressure of about 25 psi or about 50 psi or more above the pressure of the liquid media prior to dispersion in the liquid media.

12. The method of claim 1, wherein dispersing the $C_1$ substrate in the liquid media including at least water and one or more nutrients to form a multi-phase mixture comprising $C_1$ substrate bubbles dispersed in the liquid media, further comprises controlling the flow of the $C_1$ substrate to maintain a dissolved oxygen concentration of less than about 10 ppm in the multi-phase mixture in the one or more downward flow paths, in the one or more upward flow paths, or both.

13. The method of claim 1, wherein dispersing the $C_1$ substrate in the liquid media including at least water and one or more nutrients to form a multi-phase mixture comprising gas bubbles dispersed in the liquid media, further comprises controlling the flow of the $C_1$ substrate to maintain a dissolved methane concentration of less than about 5 ppm in the multi-phase mixture in the one or more downward flow paths, in the one or more upward flow paths, or both.

14. The method of claim 1, further comprising separating the multi-phase mixture removed from the one or more upward flow paths into a plurality of phases including at least a separated gas phase and a separated liquid phase.

15. The method of claim 14, further comprising reducing the pressure of the multi-phase mixture removed from the one or more upward flow paths to a fourth pressure prior to separating the multi-phase mixture.

16. The method of claim 15, further comprising generating electricity by at least partially reducing the pressure of the multi-phase mixture to a fourth pressure using one or more energy capture systems.

17. The method of claim 15, wherein the separated liquid phase includes a biomass comprising at least one of n-butanol, 1,3-butanediol, or 1,4-butanediol.

18. The method of claim 1, wherein the first velocity comprises a superficial fluid velocity of greater than about 0.1 feet per second (f/s), the second velocity comprises a bulk fluid velocity of less than about 10 feet per second (f/s), or both.

19. The method of claim 1, wherein
the vessel is a vertically arranged vessel including at least one fluid inlet connection fluidly coupled to at least a portion of the number of downward flow paths;
wherein each of the number of hollow fluid conduits providing a respective number of upward flow paths is fluidly coupled to at least one connection to remove the multiphase mixture from the vessel;
at least one gas distributor disposed adjacent at least one outlet of the number of hollow fluid conduits and in at least a portion of the number of downward flow paths; and
a number of structures disposed within at least a portion of at least one of: the number of downward flow paths or the number of upward flow paths, each of the number of structures to promote biological growth thereupon.

20. The method of claim 19, further comprising at least one first thermal transfer surface disposed at least partially in a portion of the number of downward flow paths.

21. The method of claim 19, further comprising one or more second thermal transfer surfaces disposed at least partially in at least a portion of the number of upward flow paths.

22. The method of claim 19, wherein the at least one gas distributor comprise one or more $C_1$ substrate distrubutors fluidly coupled to at least one first $C_1$ substrate inlet connection.

23. The method of claim 22, wherein the one or more $C_1$ substrate distributors comprise a second gas distributor fluidly coupled to at least one second gas inlet connection, the at least one second gas inlet connection to receive at least one oxygen containing gas.

24. The method of claim 19, wherein the at least one fluid inlet connection comprises at least one fluid connection to accept a fluid media.

25. The method of claim 24, wherein the at least one fluid inlet connection further comprises at least one fluid connection to accept a fluid media including at least one biological nutrient.

26. The method of claim 19, wherein an aggregate transverse cross-sectional area of the number of hollow fluid conduits is at least 10% of the transverse cross-sectional area of the vessel.

* * * * *